United States Patent
Ohashi

(10) Patent No.: US 9,517,472 B2
(45) Date of Patent: Dec. 13, 2016

(54) DEVICE AND METHOD FOR PROCESSING TARGET COMPONENT IN TUBE

(75) Inventor: Tetsuo Ohashi, Ibaraki (JP)

(73) Assignee: SHIMADZU CORPORATION, Kyoto (JP)

( * ) Notice: Subject to any disclaimer, the term of this patent is extended or adjusted under 35 U.S.C. 154(b) by 18 days.

(21) Appl. No.: 13/995,270

(22) PCT Filed: Jul. 13, 2011

(86) PCT No.: PCT/JP2011/065995
§ 371 (c)(1),
(2), (4) Date: Jun. 18, 2013

(87) PCT Pub. No.: WO2012/086243
PCT Pub. Date: Jun. 28, 2012

(65) Prior Publication Data
US 2013/0273552 A1   Oct. 17, 2013

(30) Foreign Application Priority Data

Dec. 21, 2010   (JP) ................................ 2010-285210

(51) Int. Cl.
| | |
|---|---|
| B03C 1/00 | (2006.01) |
| B01L 3/00 | (2006.01) |
| G01N 35/00 | (2006.01) |

(52) U.S. Cl.
CPC ............... *B03C 1/00* (2013.01); *B01L 3/5025* (2013.01); *B01J 2219/00364* (2013.01); *B01J 2219/00466* (2013.01); *B01J 2219/00468* (2013.01); *B01L 3/5082* (2013.01); *B01L 2200/0647* (2013.01); *B01L 2200/0673* (2013.01); *B01L 2300/087* (2013.01); *B01L 2300/0832* (2013.01); *B01L 2300/0861* (2013.01); *B01L 2400/043* (2013.01); *G01N 35/0098* (2013.01); *Y10T 29/49826* (2015.01)

(58) Field of Classification Search
None
See application file for complete search history.

(56) References Cited

U.S. PATENT DOCUMENTS

| | | |
|---|---|---|
| 3,313,358 A | 4/1967 | Postlewaite et al. |
| 4,487,700 A | 12/1984 | Kanter |
| 4,683,195 A | 7/1987 | Mullis et al. |
| 4,683,202 A | 7/1987 | Mullis |
| 4,786,600 A | 11/1988 | Kramer et al. |
| 4,800,159 A | 1/1989 | Mullis et al. |
| 4,965,188 A | 10/1990 | Mullis et al. |
| 5,354,688 A | 10/1994 | Francis et al. |
| 5,409,818 A | 4/1995 | Davey et al. |
| 5,455,166 A | 10/1995 | Walker |
| 5,494,810 A | 2/1996 | Barany et al. |
| 6,121,055 A | 9/2000 | Hargreaves |
| 6,951,722 B2 | 10/2005 | Mukai et al. |
| 2005/0123950 A1 | 6/2005 | Mukai et al. |
| 2005/0239100 A1 | 10/2005 | Mukai et al. |
| 2008/0160630 A1 | 7/2008 | Liu et al. |

FOREIGN PATENT DOCUMENTS

| | | |
|---|---|---|
| EP | 0 368 906 B1 | 11/1994 |
| EP | 0 623 683 B1 | 9/2000 |
| JP | 59-154362 A | 9/1984 |
| JP | 2-502405 A | 8/1990 |
| JP | 2-289596 A | 11/1990 |
| JP | 2843586 B2 | 1/1999 |
| JP | 3433929 B2 | 8/2003 |
| WO | WO-88/10315 A1 | 12/1988 |
| WO | WO-00/56877 A1 | 9/2000 |

OTHER PUBLICATIONS

Written Opinion of the International Searching Authority (PCT/ISA/237) for Application No. PCT/JP2011/065995 mailed Jul. 4, 2013.
International Search Report for the Application No. PCT/JP2011/065995 mailed Oct. 25, 2011.
"FDA Issues Another Emergency Use Authorization for Commercial H1N1 Flu Test to Quest Diagnostics' Focus Diagnostics", Focus Diagnostics Inc., Oct. 17, 2009.
"GC series Magtration Genomic DNA Whole Blood", Precision System Science Co., Ltd., Dec. 2008, Version 4.0.
Raja, Siva et al., "Technology for Automated, Rapid, and Quantitative PCR or Reverse Transcription—PCR Clinical Testing", Clinical Chemistry, 2005, vol. 51, No. 5, pp. 882-890.

*Primary Examiner* — David Thomas
(74) *Attorney, Agent, or Firm* — Cheng Law Group, PLLC

(57) ABSTRACT

The present invention provides a small and low running-cost device capable of minimizing the generation of contamination sources as much as possible while performing a series of all the desired manipulations. A device for manipulating a target component in a manipulation tube, comprising: a manipulation tube comprising a tube having an optionally-closeable open end for supplying a sample containing a target component at one end and a closed end at the other end, and a manipulation medium accommodated in the tube and having a gel layer and an aqueous liquid layer multi-layered in a longitudinal direction of the tube; magnetic particles that should transport the target component; and magnetic field applying means capable of applying a magnetic field to the manipulation tube to move the magnetic particles in the longitudinal direction of the tube.

19 Claims, 9 Drawing Sheets

← 171 bases

Lane M: 100bp Ladder Molecular Weight Marker
Lane P: Liquid after PCR Reaction (5 μL)

SEQUENCE LISTING

```
<160> NUMBER OF SEQ ID NOS: 4

<210> SEQ ID NO 1
<211> LENGTH: 24
<212> TYPE: DNA
<213> ORGANISM: Artificial
<220> FEATURE:
<223> OTHER INFORMATION: synthetic primer

<400> SEQUENCE: 1
gcgctgccaa ggctgtgggc aagg                                            24

<210> SEQ ID NO 2
<211> LENGTH: 24
<212> TYPE: DNA
<213> ORGANISM: Artificial
<220> FEATURE:
<223> OTHER INFORMATION: synthetic primer

<400> SEQUENCE: 2
ggccctccga cgcctgcttc acca                                            24

<210> SEQ ID NO 3
<211> LENGTH: 22
<212> TYPE: DNA
<213> ORGANISM: Artificial
<220> FEATURE:
<223> OTHER INFORMATION: synthetic primer
```

```
<400> SEQUENCE: 3
gaccratcct gtcacctctg ac                                              22

<210> SEQ ID NO 4
<211> LENGTH: 24
<212> TYPE: DNA
<213> ORGANISM: Artificial
<220> FEATURE:
<223> OTHER INFORMATION: synthetic primer

<400> SEQUENCE: 4
agggcattyt ggacaaakcg tcta                                            24
```

DEVICE AND METHOD FOR PROCESSING TARGET COMPONENT IN TUBE

TECHNICAL FIELD

The present invention relates to a device and a method for manipulating a target component with the use of a gel. More specifically, the present invention relates to a device and a method capable of subjecting a target component to various manipulations in a hermetically-sealable tube by manipulating magnetic particles in the tube with a magnetic field from the outside of the tube. Even more specifically, the present invention relates to a device and a method capable of performing extraction, purification, synthesis, elution, separation, recovery, and analysis of a target component by manipulating magnetic particles in a tubule in which a reagent liquid is accommodated with the use of an oil gel.

BACKGROUND ART

Water-insoluble microparticles having a diameter of a dozen or so micrometers to 0.5 μm can be used to extract/purify, separate, and recover a target component by allowing the surface of the microparticles to have various chemical affinities. Further, such microparticles can also be used to recover target cells by allowing them to identify a specific cell-surface molecule. Therefore, microparticles having a functional molecule introduced onto their surface depending on the type of target are commercially available. Among these microparticles, those made of a ferromagnetic material such as iron oxide allow a target component to be recovered by a magnet without the need of centrifugation, and are therefore advantageous for automation of chemical extraction/purification.

For example, a system is commercially available, which performs a series of processes from extraction of nucleic acid from cells to analysis by gene amplification reaction in a single device. For example, GeneXpert System available from Cepheid (USA) can perform a series of processes from nucleic acid extraction to analysis by gene amplification reaction in a single cartridge-type device and can treat simultaneously up to 16 samples (the technical contents of GeneXpert System are described in Non-Patent Document 1). Further, for example, Simplexa (Non-Patent Document 2) available from 3M can perform a series of processes from nucleic acid extraction to PCR in a single disk-shaped device in which 12 samples can be immobilized.

On the other hand, magnetic particles are commercially available as one of reagents supplied as an extraction/purification kit. Such a kit includes two or more reagents contained in separate containers, and when the kit is used, each of the reagents is dealt and dispensed by a user with a pipette or the like. Even in the case of a currently commercially available automated device, dispensing of liquid is performed by mechanically operating a pipette. For example, a system (Non-Patent Document 3) is commercially available from Precision System Science Co. Ltd., which uses magnetic particles to extract nucleic acid.

PRIOR ART DOCUMENTS

Non-Patent Documents

Non-Patent Document 1: Clinical Chemistry 51: 882-890, Mar. 3, 2005

Non-Patent Document 2: "FDA Issues Another Emergency Use Authorization for Commercial H1N1 Flu Test to Quest Diagnostics' Focus Diagnostics", Focus Diagnostics Inc., Oct. 17, 2009

Non-Patent Document 3: "GC series Magtration Genomic DNA Whole Blood" Precision System Science Co., Ltd., December 2008

SUMMARY OF THE INVENTION

Problems to be Solved by the Invention

In general, commercially-available magnetic particles allow separation and recovery of a target component or specific cells from a sample, but another system such as a real-time PCR device, a mass spectrometer, or a flow cytometer is required to analyze a recovered substance.

Commercially-available systems that perform a series of processes from extraction of nucleic acid from cells to analysis by gene amplification reaction in a single device can simultaneously treat only a small number of samples, and are not suitable for practical use because the device itself is complicated and its production cost is high.

For example, in the case of GeneXpert System available from Cepheid (USA), particularly, its device is complicated and requires high cost (42 US dollars per sample). Further, the device is large in size, and therefore the entire system is also large and cannot be easily moved for use. Particularly, this system is not suitable for POCT (Point of Care Testing) intended to treat a relatively small number of samples.

Further, for example, in the case of Simplexa available from 3M, the number of samples in one disk is fixed to 12, and therefore the number of samples to be treated cannot be arbitrarily set.

Pipetting necessarily performed when an extraction/purification kit including magnetic particles as one of reagents is used involves the generation of aerosols. This increases the risk of contamination that interferes with analysis. The same shall apply for an automated device in which dispensing of liquid is performed by mechanical pipetting. In this case, contamination sources are accumulated in the device by the generation of aerosols, and therefore the device needs to be periodically washed. However, the automated device having a pipette dispensing system has a complicated structure and therefore it is difficult to completely remove contamination sources.

The system commercially available from Precision System Science Co., Ltd., which uses magnetic particles to extract nucleic acid, can be used until the end of recovery of purified nucleic acid, but analysis by gene amplification reaction or the like needs to be performed in another system such as a real-time PCR device. Further, this system always involves the risk of contamination because dispensing is performed by a pipette-type dispenser in an open system.

It is an object of the present invention to provide a small and low running-cost device capable of minimizing the generation of contamination sources as much as possible while performing a series of all the desired manipulations in a completely hermetically sealed state.

It is an object of the present invention to provide a small and low running-cost device capable of, for example, extracting/purifying a target component in a completely hermetically sealed container, or performing also analysis after the extraction/purification in the same container while maintaining a hermetically sealed state.

Means for Solving the Problems

The present inventor has intensively studied and as a result has found that the above object of the present invention can be achieved, without using a dispenser that accompanies the generation of aerosols, by a hermetically sealable tubule (capillary), which accommodates one or more liquid reagents in a compartment(s) separated by a water-insoluble gel material and magnetic particles present in the liquid reagent accommodated in the tubule, and magnetic field applying means that can be manipulated on the outside of the tubule. This finding has led to the completion of the present invention.

The present invention includes the following inventions.

(1) A device for manipulating a target component in a manipulation tube, comprising:

a manipulation tube comprising a tube having an optionally-closeable open end for supplying a sample containing a target component at one end and a closed end at the other end, and a manipulation medium accommodated in the tube and having a gel layer and an aqueous liquid layer alternately layered in a longitudinal direction of the tube;

magnetic particles that should capture and transport the target component; and magnetic field applying means capable of applying a magnetic field to the manipulation tube to move the magnetic particles in the longitudinal direction of the manipulation tube.

It is preferred that the open end is openably/closably closed in entirety or in part of the open end. Preferred examples of such an open end are shown in FIGS. 1(2) and 1(3).

(2) The device according to (1), wherein the tube has an approximate inner diameter of 0.1 mm to 5 mm.

(3) The device according to (1) or (2), wherein the magnetic field applying means can move the magnetic particles in the longitudinal direction of the manipulation tube from an outside of the manipulation tube.

(4) The device according to any one of (1) to (3), further comprising holding means capable of holding the manipulation tube almost vertically in such a manner that the open end faces upward.

(5) The device according to (4), wherein the holding means is a holding substrate having a plurality of holding holes capable of holding the closed end of the manipulation tube.

An example of the holding means serving as the holding substrate in the above (5) is shown by a reference sign 51 in FIGS. 5 and 7.

(6) The device according to (4) or (5), wherein the holding means has a temperature control function.

(7) The device according to any one of (4) to (6), wherein the holding means has a recess allowing the magnetic field applying means to be moved in the longitudinal direction of the manipulation tube.

An example of the holding means having a recess in the above (7) is shown by a reference sign 51 in FIG. 7.

(8) The device according to any one of (4) to (7), wherein the holding means has an optical detection port.

(9) The device according to any one of (1) to (8), wherein the magnetic field applying means has a system that controls movement of a magnetic field in the longitudinal direction of the manipulation tube and strength of the magnetic field.

(10) The device according to any one of (1) to (9), wherein the magnetic field applying means has a temperature control function.

(11) The device according to any one of (5) to (10), wherein the magnetic field applying means comprises a movable substrate capable of moving in the longitudinal direction of the manipulation tube, and a plurality of magnetic sources held in the movable substrate.

An example of the magnetic field applying means in the above (11) is shown as a movable magnetic plate 53 in FIG. 5.

(12) The device according to (11), wherein the system that controls movement of a magnetic field in the longitudinal direction of the manipulation tube and strength of the magnetic field simultaneously moves the plurality of magnetic sources in the movable substrate.

An example of the movable substrate having the system in the above (12) is shown in FIG. 6.

(13) The device according to any one of (1) to (12), wherein the magnetic particles have an ability to bind to or adsorb to nucleic acid as the target component, and the manipulation medium includes an aqueous liquid layer composed of a liquid that liberates the nucleic acid to bind or adsorb the nucleic acid to the magnetic particles and/or an aqueous liquid layer composed of a liquid for washing the magnetic particles.

(14) The device according to (13), wherein the manipulation medium further includes an aqueous liquid layer composed of a nucleic acid amplification reaction liquid; or an aqueous liquid layer composed of a reverse transcription reaction liquid and an aqueous liquid layer composed of a nucleic acid amplification reaction liquid.

(15) The device according to any one of (1) to (14), wherein the tube is integrally formed.

(16) The device according to any one of (1) to (15), wherein the manipulation tube has a manipulation part A and a recovery part B;

the tube constituting the manipulation tube has a manipulation tube portion a and a recovery tube portion b corresponding to the manipulation part A and the recovery part B, respectively;

the manipulation part A comprises the tube portion a, and the manipulation medium accommodated in the tube portion a; and the recovery part B comprises the tube portion b, and a recovery medium accommodated in the tube portion b and including at least one of an aqueous liquid layer and a gel layer.

An example of the manipulation tube in the above (16) is shown in FIG. 1(3).

(17) The device according to (16), wherein the manipulation tube portion a and the recovery tube portion b are separable from each other.

(18) The device according to any one of (1) to (17), wherein the tube is made of a material selected from the group consisting of polyethylene, polypropylene, fluorine resin, polyvinyl chloride, polystyrene, polycarbonate, acrylonitrile butadiene styrene copolymer (ABS resin), acrylonitrile styrene copolymer (AS resin), acrylic resin, polyvinyl acetate, polyethylene terephthalate, cyclic polyolefin, and glass.

(19) A method for producing the manipulation tube included in the device according to (1), the method comprising a step of alternately layering an aqueous liquid layer and a gel layer in a tube having an open end at one end and a closed end at the other end.

(20) A method for producing the manipulation tube included in the device according to (16), the method comprising the steps of:

(i) producing a manipulation part A by alternately layering a gel layer and an aqueous liquid layer in a manipulation tube a, having open ends at both ends, from one of the ends of the manipulation tube a;

(ii) producing a recovery part B by allowing a recovery tube b, having an open end at one end and a closed end at the other end, to accommodate an aqueous liquid or a gel, or by alternately layering an aqueous liquid layer and a gel layer in the recovery tube b; and (iii) connecting the one of the ends of the manipulation tube a of the manipulation part A and the open end of the recovery tube b of the recovery part B to each other.

The step (i) of the method according to the above (20) is schematically shown in FIG. 2.

(21) A method for manipulating a target component by using the device according to (1), the method comprising the following steps of:

(i) obtaining an aqueous liquid mixture containing a sample containing a target component, magnetic particles, and an aqueous liquid, in an uppermost layer in the manipulation tube;

(ii) allowing the magnetic field applying means to produce a magnetic field to transport the magnetic particles together with the target component from the uppermost layer composed of the aqueous liquid mixture through the gel layer to an aqueous liquid layer adjacent to the gel layer;

(iii) performing desired treatment in the aqueous liquid layer;

(iv) allowing the magnetic field applying means to produce a magnetic field to transport the magnetic particles together with the target component from the aqueous liquid layer to another aqueous liquid layer;

(v) performing desired treatment in the another aqueous liquid layer;

(vi) repeating the steps (iv) and (v), if necessary; and (vii) transporting the magnetic particles together with the target component to a lowermost layer in the manipulation tube.

(22) The method according to (21), wherein the number of the manipulation tubes is two or more, and the transport by the magnetic particles is simultaneously performed in the manipulation tubes.

(23) The method according to (21) or (22), wherein the target component is nucleic acid;

in the step (i), the aqueous liquid contained in the aqueous liquid mixture constituting the uppermost layer is a liquid that liberates the nucleic acid to bind or adsorb the nucleic acid to the magnetic particles, and nucleic acid extraction is performed in the aqueous liquid; and in the steps (ii) to (vi), at least one of the aqueous liquid layers is composed of a liquid for washing the magnetic particles, and nucleic acid purification is performed in the washing liquid by removing a contaminant generated together with the liberated nucleic acid.

(24) The method according to (23), wherein in the step (vii), the lowermost layer is composed of a nucleic acid amplification reaction liquid, and target nucleic acid in the purified nucleic acid is amplified in the nucleic acid amplification reaction liquid.

In the above (24), when the nucleic acid is RNA, a layer directly above the lowermost layer composed of the nucleic acid amplification reaction liquid is composed of a reverse transcription reaction liquid.

(25) The method according to (24), wherein a product of the nucleic acid amplification reaction is optically detected in real time.

Effects of the Invention

According to the present invention, it is possible to provide a small and low running-cost device capable of minimizing the generation of contamination sources as much as possible while performing a series of all the desired manipulations.

According to the present invention, it is possible to provide a small and low running-cost device capable of, for example, extracting/purifying a target component in a completely hermetically sealed container, or performing also analysis after the extraction/purification in the same container while maintaining a hermetically sealed state.

MODES FOR CARRYING OUT THE INVENTION

[1. Manipulation of Target Component]
[1-1. Target Component]

A target component to be manipulated in the present invention is not particularly limited as long as it can be usually manipulated in an aqueous liquid, an emulsion, or a hydrogel, and may be either an in-vivo component or an in-vitro component. The in-vivo component includes biological molecules such as nucleic acid (including DNA and RNA), protein, lipid, and sugar. The in-vitro component includes nonbiological molecules such as artificially (chemically or biochemically) modified products, labeled products, or mutants of the above biological molecules, naturally-occurring nonbiological molecules, and any other components that can be manipulated in an aqueous liquid.

The target component may usually be provided in the form of a target component-containing sample. Examples of such a sample include living body-derived samples such as animal or plant tissue, body fluid, and body waste and biological molecule-containing objects such as cells, protozoa, fungi, bacteria, and viruses. Examples of the body fluid include blood, sputum, spinal fluid, saliva, and milk, and examples of the body waste include feces, urine, and sweat, and they may be used in combination. Examples of the cells include white blood cells and platelets in blood and exfoliated mucosal cells such as buccal cells, and they may be used in combination. These samples may be obtained as clinical swabs. The above sample may be prepared in the form of, for example, a cell suspension, a homogenate, or a mixture liquid with a cell lysis liquid.

The target component-containing sample may be obtained by performing treatment such as modification, labeling, fragmentation, or mutation on the above sample.

The target component-containing sample may be a sample prepared by further performing appropriate pretreatment on the above sample in advance. An example of the pretreatment includes treatment performed to extract and separate a target component or a target component-containing object from the target component-containing sample and purify it. However, such pretreatment can be performed in a device according to the present invention, and is therefore not always required to be performed in advance before the target component-containing sample is supplied into the device. By performing pretreatment in the device according to the present invention, it is possible to avoid contamination that is an issue of concern for conventional sample pretreatment.

[1-2. Manipulation]

[1-2-1. Manipulation Mode]

Figure 1:
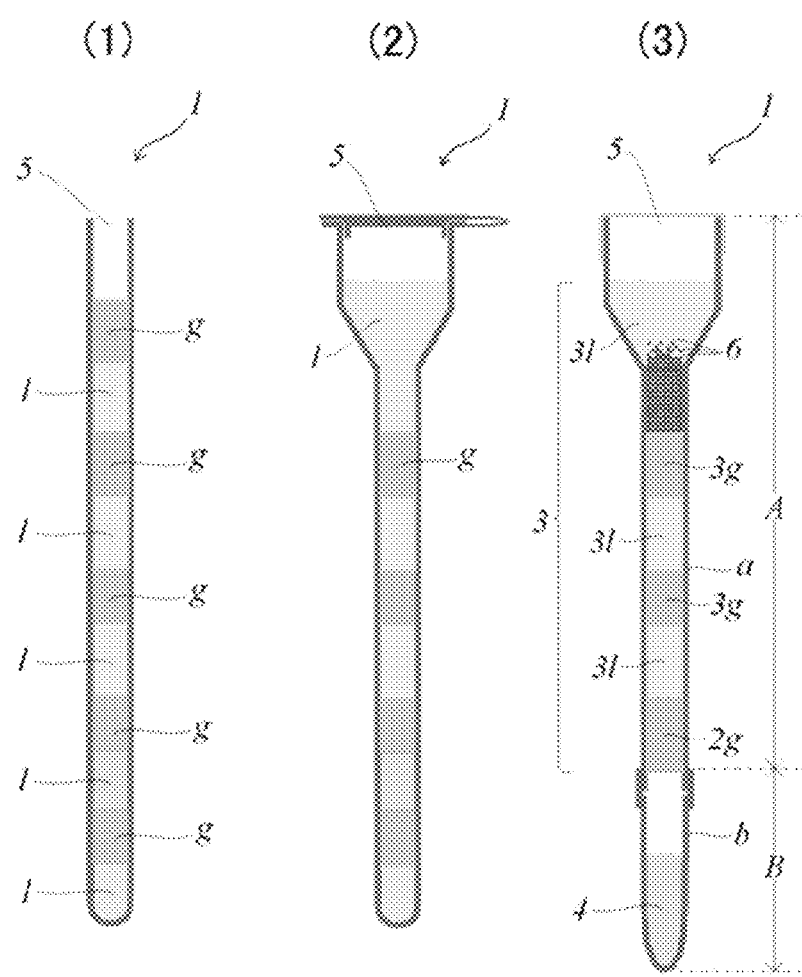
FIG. 1 is a longitudinal sectional view of an example of a manipulation tube according to the present invention.

In the present invention, a target component-containing sample is supplied into a manipulation tube illustrated by a reference sign 1 in FIG. 1, and the target component is manipulated in the manipulation tube. The manipulation of the target component in the present invention includes subjecting the target component to various treatments and transporting the target component between two or more environments in which various treatments are performed.

As will be described later, the manipulation tube accommodates a gel layer and an aqueous liquid layer. For example, in an embodiment illustrated in FIG. 1, layers shown by reference signs 2g and 3g are composed of a gel (gel plug), and layers shown by reference sign 31 are composed of an aqueous liquid. A layer shown by a reference sign 4 may be composed of an aqueous liquid or may be composed of a hydrogel as long as the aqueous liquid can maintain a gel state. Such an aqueous liquid or hydrogel creates an environment in which the treatment of the target component is performed.

Therefore, more specifically, the manipulation of the target component in the present invention includes subjecting the target component to treatment in an aqueous liquid or a hydrogel; and transporting the target component between two or more environments, in which treatments are performed, through a gel plug.

[1-2-2. Treatment of Target Component]

The treatment to which the target component is subjected includes treatment that involves a material change of the target component and treatment that involves a physical change of the target component.

The treatment that involves a material change of the target component includes any treatment by which a different substance is newly produced by forming or breaking a bond between substrates. Specific examples thereof include a chemical reaction and a biochemical reaction.

The chemical reaction includes any reaction that involves chemical combination, decomposition, oxidation, or reduction. In the present invention, the chemical reaction usually includes reaction performed in the aqueous liquid. The biochemical reaction also includes any reaction that involves a material change of a biological material, and usually refers to an in-vitro reaction. Examples thereof include reactions based on the synthetic system, metabolic system, and immune system of biological materials such as nucleic acid, protein, lipid, and sugar.

The treatment that involves a physical change of the target component includes any treatment that does not involve the above-described material change. Specific examples thereof include denaturation (e.g., in a case where the target component is a biological polymer containing nucleic acid or protein or another polymer), lysis, mixing, emulsification, and dilution of the target component.

Therefore, the treatment in the present invention makes it possible to perform processes such as extraction, purification, synthesis, elution, separation, recovery, and analysis of the target component. By performing these processes, it is possible to finally isolate, detect, identify, and the like of the target component.

It is to be noted that, the treatment in the present invention may appropriately include not only treatment of interest (treatment performed in processes capable of directly obtaining effects such as isolation, detection, and identification of the target component) but also pretreatment and/or aftertreatment associated with the treatment of interest. For example, in a case where the target component is nucleic acid, the process of nucleic acid amplification reaction, the process of nucleic acid amplification reaction and amplified product analysis, or the like may be performed, but as pretreatment of such a process, extraction (cell lysis) and/or purification (washing) of nucleic acid from a nucleic acid-containing sample is/are essential, and there is a case where the recovery of an amplified product or the like is performed as aftertreatment.

[1-2-3. Transport of Target Component]

The target component is transported by magnetic particles and magnetic field applying means. The magnetic particles are present in the manipulation tube during manipulation, and can be moved in the manipulation tube while capturing the target component bound or adsorbed to their surface to transport the target component. The magnetic particles can be dispersed in the aqueous liquid layer in the manipulation tube, and are usually agglomerated in the aqueous liquid layer by allowing the magnetic field applying means to produce a magnetic field on the outside of the manipulation tube. The agglomerated magnetic particles can be moved by varying the magnetic field produced by the magnetic field applying means on the outside of the manipulation tube. The agglomerated magnetic particles can be moved into the gel layer. By utilizing the thixotropic properties (thixotropy) of the gel that will be described later in 3-2-3, it is possible that the agglomerated magnetic particles pass through the gel layer without breaking the gel layer. In the gel, the agglomerated magnetic particles are accompanied by the target component bound or adsorbed thereto. Strictly speaking, the agglomerated magnetic particles are coated with a very small amount of the aqueous liquid. That is, the agglomerated magnetic particles may be accompanied by a component other than the target component. However, the amount of the aqueous liquid coating the agglomerated magnetic particles is very small, and therefore it can be said that the clumped magnetic particles are accompanied by little aqueous liquid. This makes it possible to very efficiently transport the target component.

[2. Manipulation Tube]

[2-1. Structure of Manipulation Tube]

The device according to the present invention has a manipulation tube. The structure of the manipulation tube will be described with reference to FIG. 1 (in the following description, "upper" and "lower" refer to the upper side and the lower side of FIG. 1, respectively). A tube constituting the manipulation tube has an open upper end for charging a sample, and from the viewpoint of contamination, the open end is preferably closable. A lower end of the tube is closed. The tube constituting the manipulation tube usually has an almost circular cross section, but tubes having other cross-sectional shapes are not excluded. The tube accommodates a manipulation medium having aqueous liquid layers 1 and gel layers g alternately multilayered in the longitudinal direction of the tube. It is to be noted that FIG. 1 shows three embodiments (1) to (3) different in the upper and lower portions of the manipulation tube. However, the combination of the upper and lower portions can be arbitrarily made and is not limited to those shown in FIGS. 1(1) to 1(3).

The upper open end of the tube is a sample supply portion 5 for supplying a target component-containing sample, and the sample supply portion 5, which is an open end, may be temporarily opened (FIG. 1(1)) or openably closed in its entirety (FIG. 1(2)) or in part. An example of the sample supply portion 5 openably closed in part is one using a septum having the function of a check valve (FIG. 1(3)). In this case, a sample can be supplied by puncture using a syringe needle in a state close to a hermetically sealed state. Closing the sample supply portion 5 that is an open end is preferred in that a completely closed system can be formed. The fact that a completely closed system can be formed is very effective because contamination form the outside during manipulation can be prevented. The inner diameter of the sample supply portion 5 may be the same as that of a tube portion a housing the manipulation medium having the gel layers and the aqueous liquid layers (FIG. 1(1)), or the sample supply portion 5 may be appropriately formed to have a larger inner diameter from the viewpoint of manipulability during the supply of a sample (FIG. 1(2) or 1(3)).

In each of the embodiments illustrated in FIGS. 1(1) and 1(2), the tube is integrally formed. In the embodiment illustrated in FIG. 1(3), the tube is constituted from a manipulation tube portion a, and a recovery tube portion b. The manipulation tube portion a has open upper and lower ends. The recovery tube portion b has an open upper end and a closed lower end. The manipulation tube portion a and the recovery tube portion b are connected to each other through one of the ends of the tube portion a and the open end of the tube portion b. The manipulation tube portion a and the recovery tube portion b may be formed to be able to separate from each other, or may be formed without considering separation (i.e., may be formed to be unable to separate from each other).

The manipulation tube portion a accommodates a gel layer 2g that closes one of its ends, and multiple layers layered on the gel layer 2g, that is, a manipulation medium 3. The manipulation medium 3 is constituted from aqueous liquid layers 31 and gel layers 3g alternately multilayered. A part constituted from the manipulation tube portion a and the manipulation medium accommodated in the manipulation tube portion a is referred to as a manipulation part A.

The recovery tube portion b accommodates a recovery medium 4 containing at least one of an aqueous liquid and a gel. A part constituted from the recovery tube portion b and the recovery medium 4 accommodated in the recovery tube portion b is referred to as a recovery part B.

The manipulation part A and the recovery part B may be provided in a state where they are connected to each other, or a state where they are separated from each other.

[2-2. Size of Manipulation Tube]

The approximate inner diameter of the tube constituting the manipulation tube is, for example, 0.1 mm to 5 mm, preferably 1 to 2 mm. By setting the approximate inner diameter to a value within the above range, it is possible that the manipulation tube has excellent manipulability. If the approximate inner diameter is less than the above range, the wall thickness of the tube must be increased in order to maintain strength, which increases the distance between magnetic particles and a magnet and makes it difficult for magnetic force to reach the magnetic particles, and therefore there is a possibility that problems with manipulation are caused. On the other hand, if the inner diameter of the tube exceeds the above range, there is a tendency that the multi-layered gel layers and aqueous liquid layers constituting the manipulation medium are easily disturbed under the influence of external force or gravity, or the like. It is to be noted that in the present invention, tubes having an inner diameter of 0.1 mm or less are not excluded as long as a capillary material can withstand high-precision processing.

The longitudinal length of the manipulation tube is, for example, 1 to 30 cm, preferably 5 to 15 cm.

It is to be noted that as shown in FIGS. 1(2) and 1(3), when the reagent supply portion 5 is formed to have a larger inner diameter, the approximate inner diameter of the sample supply portion 5 may be larger than the above range but 10 mm or less, preferably 5 mm or less. Allowing the reagent supply portion to have a larger inner diameter is preferred from the viewpoint of workability during the supply of a reagent. If such a larger inner diameter exceeds the above range, the device tends to be poor in accumulation properties because, for example, when the two or more manipulation tubes are simultaneously treated, interference occurs between the manipulation tubes.

[2-3. Material of Tube]

A material of the tube constituting the manipulation tube is not particularly limited. Examples thereof include materials that make the inner wall of the tube, which serves as a carrying surface, smooth and water repellent in order to reduce transfer resistance at the time when a target component and a trace amount of liquid are moved together with magnetic particles in the gel layer. Examples of the material that imparts such properties include resin materials such as polyethylene, polypropylene, fluorine resin (Teflon (registered trademark)), polyvinyl chloride, polystyrene, polycarbonate, acrylonitrile butadiene styrene copolymer (ABS resin), acrylonitrile styrene copolymer (AS resin), acrylic resin, polyvinyl acetate, polyethylene terephthalate, and cyclic polyolefin. Such a resin material is preferred in that the manipulation tube can have high toughness and that, even when the manipulation tube is dropped or bent, the layers in the manipulation tube are less likely to be disturbed. If necessary, the material of the tube may be glass from the viewpoint of transparency, heat resistance, and/or processability.

The reagent supply portion 5, the manipulation tube portion a, and the recovery tube portion b may be made of the same material or different materials.

[2-4. Physical Properties of Tube]

The material of the tube preferably has optical transparency from the viewpoint of visibility during manipulation or from the viewpoint of performing optical detection to measure, for example, changes in absorbance, fluorescence, chemiluminescence, bioluminescence, or refractive index from the outside of the tube.

The carrying surface constituting the inner wall of the tube is preferably a smooth surface and particularly preferably has a surface roughness Ra of 0.1 µm or less, because a small amount of liquid lump containing a target component is moved together with magnetic particles in the gel layer.

For example, magnetic particles are moved while being pressed against the carrying surface when a small amount of liquid lump containing a target component is moved by varying a magnetic field with bringing a permanent magnet close to the tube on the outside of the tube, but allowing the carrying surface to have a surface roughness Ra of 0.1 μm or less makes it possible for the magnetic particles to sufficiently follow the varying magnetic field.

[3. Accommodated products of Manipulation Tube]

[3-1. Manipulation Medium]

The manipulation tube accommodates at least, as a manipulation medium, multiple layers in which a layer compose of an aqueous liquid and a layer composed of a gel are alternately multilayered. An uppermost layer of the multiple layers may be a gel layer (FIG. 1(1)) or an aqueous liquid layer (FIGS. 1(2) and 1(3)). When the uppermost layer is an aqueous liquid layer, magnetic particles 6 may be contained in this layer (FIG. 1(3)) or may not be contained in this layer (FIGS. 1(1) and 1(2)). A lowermost layer of the multiple layers may be an aqueous liquid layer (FIGS. 1(1) to 1(3)) or a gel layer.

As shown in FIGS. 1(1) and 1(2), when the tube constituting the manipulation tube is integrally formed, all the layers accommodated in the tube may be in contact with each other.

As shown in FIG. 1(3), when the tube constituting the manipulation tube is constituted from the manipulation tube portion a and the recovery tube portion b, the recovery tube portion b may accommodate only an aqueous liquid as a recovery medium, or may accommodate only a gel, or may accommodate multiple layers in which an aqueous liquid layer and a gel layer are alternately multilayered. The gel layer 2g accommodated in the manipulation tube portion a as a lowermost layer, and the aqueous liquid or the gel accommodated in the recovery tube portion b or an uppermost layer of the multiple layers accommodated in the recovery tube portion b may be in contact with each other or may not be in contact with each other with a gas layer interposed therebetween (FIG. 1(3)).

The number and order of the layers accommodated in the tube are not particularly limited and may be appropriately determined by those skilled in the art based on the number and order of manipulation processes to which a target component is subjected.

The respective aqueous liquid layers accommodated in one manipulation tube are preferably composed of two or more different aqueous liquids. As the different aqueous liquids constituting the layers, liquids that create environments necessary for treatment or reaction processes to which a target component is subjected can be used in order from the upper end of the manipulation tube.

The respective gel layers accommodated in one manipulation tube may be composed of different gels or the same gel. For example, when treatment or reaction is performed by heating in part of the aqueous liquid layers among one or more of the aqueous liquid layers, only the gel layers adjacent to the one or more aqueous liquid layers may be composed of a gel that has a high sol-gel transition point and therefore can maintain a gel state or an intermediate state between gel and sol even at temperatures necessary for the heating, and the other gel layers may be composed of a gel having a relatively low sol-gel transition point. Further, a gel having appropriate properties may be appropriately selected by those skilled in the art depending on the properties or volume of the aqueous liquid constituting the aqueous liquid layer adjacent to the gel.

The gel layer plays a role as a plug (gel plug) provided on either side of the aqueous liquid layer in the longitudinal direction of the manipulation tube to separate the aqueous liquid layer. The thickness of the gel layer can be appropriately determined by those skilled in the art in consideration of the inner diameter or length of the tube, the amount of magnetic particles carried by magnetic field applying means, or the like, so that the gel layer can function as a plug. For example, the thickness may be, for example, 1 to 20 mm, preferably 3 to 10 mm. If the thickness is less than the above range, the gel layer tends to lack strength as a plug. If the thickness exceeds the above range, the length of the manipulation tube is increased so that manipulability, and device durability and housing performance tend to be poor.

The aqueous liquid layer provides an environment for treatment or reaction to which a target component-containing sample is subjected. The thickness thereof can be appropriately determined by those skilled in the art in consideration of the inner diameter or length of the tube, the amount of a target component, the type of treatment or reaction to which a target component is subjected, or the like so that the aqueous liquid can be given in such an amount that desired treatment or reaction can be performed on the target component. The thickness may be, for example, 0.5 to 30 mm, preferably 3 to 10 mm. If the thickness is less than the above range, there is a case where treatment or reaction cannot be sufficiently performed on a target component, and in addition, there is a fear that the plug is put into a droplet state so that magnetic particles cannot coalesce with a reagent. On the other hand, if the thickness exceeds the above range, the aqueous liquid layer is often relatively thicker than the gel layer, and therefore there is a possibility that the same problem as the gel plug arises, and in addition, when the specific gravity of the aqueous liquid is larger than that of the gel, the multiple layers tend to easily collapse.

On the other hand, when the gel layer is composed of a hydrogel, the hydrogel layer not only can play the role of a partition between reagents but also can provide an environment for treatment or reaction to which a target component-containing sample is subjected. In this case, the thickness of the hydrogel layer may be larger than that of the aqueous liquid layer.

[3-2. Type of Gel]

The gel layer is composed of a chemically-inactive substance that is insoluble or poorly-soluble in a liquid constituting the aqueous liquid layer when layered on the aqueous liquid in the tube. The "insoluble or poorly-soluble in a liquid" means that the degree of solubility in a liquid at 25° C. is approximately 100 ppm or less. The "chemically-inactive substance" refers to a substance having no chemical influence on a target component and the aqueous liquid or the hydrogel during the manipulation of the target component (i.e., during the treatment of the target component in the aqueous liquid or the hydrogel and the transport of the target component through the gel plug). In the present invention, the gel in the present invention includes both an organogel and a hydrogel.

[3-2-1. Organogel]

An organogel is usually obtained by gelating a water-insoluble or poorly water-soluble liquid substance with addition of a gelating agent.

[3-2-1-1. Water-Insoluble or Poorly Water-Soluble Liquid Substance]

As the water-insoluble or poorly water-soluble liquid substance, an oil may be used which is in a liquid state at ordinary temperature (20° C.±15° C.) and has a degree of solubility in water at 25° C. of about 100 ppm or less. For example, the oil may be used by combining one or two or more oils from the group consisting of liquid oils and fats, ester oils, hydrocarbon oils, and silicone oils.

Examples of the liquid oils and fats include linseed oil, camellia oil, macadamia nut oil, corn oil, mink oil, olive oil, avocado oil, sasanqua oil, castor oil, safflower oil, persic oil, cinnamon oil, jojoba oil, grape oil, sunflower oil, almond oil, rapeseed oil, sesame oil, wheat germ oil, rice germ oil, rice bran oil, cottonseed oil, soybean oil, peanut oil, tea seed oil, evening primrose oil, egg-yolk oil, liver oil, coconut oil, palm oil, and palm kernel oil.

Examples of the ester oils include octanoates such as cetyl octanoate, laurates such as hexyl laurate, myristates such as isopropyl myristate and octyldodecyl myristate, palmitates such as octyl palmitate, stearates such as isocetyl stearate, isostearates such as isopropyl stearate, isopalmitates such as octyl isopalmitate, oleates such as isodecyl oleate, adipates such as isopropyl adipate, sebacates such as ethyl sebacate, malates such as isostearyl malate, glycerin trioctanoate, and glycerin triisopalmitate.

Examples of the hydrocarbon oils include pentadecane, hexadecane, octadecane, mineral oil, and liquid paraffin.

Examples of the silicone oils include dimethyl polysiloxane, methylphenyl polysiloxane, other phenyl group-containing silicone oils, and methylhydrogen polysiloxane.

[3-2-1-2. Gelating Agent]

The gelating agent may be used by combining one or two or more oil gelating agents selected from the group consisting of hydroxyl fatty acids, dextrin fatty acid esters, and glycerin fatty acid esters.

The hydroxyl fatty acids are not particularly limited as long as they are fatty acids having a hydroxyl group. Specific examples thereof include hydroxymyristic acid, hydroxypalmitic acid, dihydroxypalmitic acid, hydroxystearic acid, dihydroxystearic acid, hydroxymargaric acid, ricinoleic acid, ricinelaidic acid, and linolenic acid. Among them, hydroxystearic acid, dihydroxystearic acid, and ricinoleic acid are particularly preferred. These hydroxyl fatty acids may be used singly or in combination of two or more of them. Further, animal and plant oil fatty acids as mixtures of two or more of them (e.g., castor oil fatty acid and hydrogenated castor oil fatty acid) can also be used as the hydroxyl fatty acids.

Examples of the dextrin fatty acid esters include dextrin myristate (manufactured by Chiba Flour Milling Co., Ltd., under the trade name of "Rheopearl MKL"), dextrin palmitate (manufactured by Chiba Flour Milling Co., Ltd., under the trade names of "Rheopearl KL" and "Rheopearl TL"), dextrin palmitate/2-ethylhexanoate (manufactured by Chiba Flour Milling Co., Ltd., under the trade name of "Rheopearl TT").

Examples of the glycerin fatty acid esters include glyceryl behenate, glyceryl octastearate, and glyceryl eicosanoate, and they may be used in combination of at least one type. Specific examples thereof include "TAISET 26" (manufactured by Taiyo Kagaku Co., Ltd.) containing 20% glyceryl behenate, 20% glyceryl octastearate, and 60% hydrogenated palm oil and "TAISET 50" (manufactured by Taiyo Kagaku Co., Ltd.) containing 50% glyceryl behenate and 50% glyceryl octastearate.

The gelating agent to be added to the water-insoluble or poorly water-soluble liquid substance can be used in an amount corresponding to, for example, 0.1 to 0.5 wt %, 0.5 to 2 wt %, or 1 to 5 wt % of the total weight of the liquid substance. However, the amount of the gelating agent is not limited thereto and may be appropriately determined by those skilled in the art to the extent that a desired gel and sol state can be achieved.

A gelation method can be appropriately determined by those skilled in the art. More specifically, a water-insoluble or poorly water-soluble liquid substance is heated, and a gelating agent is added to and completely dissolved in the heated liquid substance and then cooled so that the liquid substance can be gelated. The heating temperature may be appropriately determined in consideration of the physical properties of the liquid substance and the gelating agent used. For example, there is a case where the heating temperature is preferably about 60 to 70° C. When the gelating agent is dissolved in the heated liquid substance, the gelating agent and the liquid substance may be preferably gently mixed. The cooling is preferably performed slowly. For example, the cooling may be performed over about 1 to 2 hours. For example, the cooling may be completed when the temperature of the liquid substance is reduced to ordinary temperature (20° C.±15° C.) or lower, preferably 4° C. or lower. An example of a mode to which a preferred mode of the gelation method is applied includes a mode where the above-mentioned TAISET 26 (manufactured by Taiyo kagaku Co., Ltd.) is used.

[3-2-2. Hydrogel]

As the hydrogel, hydrogels may be used which are prepared by equilibrium swelling of hydrogel materials such as gelatin, collagen, starch, pectin, hyaluronic acid, chitin, chitosan, alginic acid, and derivatives thereof in water or an aqueous liquid. Among these hydrogels, a hydrogel prepared from gelatin is preferably used. Further, the hydrogel may be obtained by chemically-crosslinking the above hydrogel material or by treating the above hydrogel material with a gelating agent (e.g., a salt of alkali metal or alkaline earth metal such as lithium, potassium, or magnesium, a salt of transition metal such as titanium, gold, silver, or platinum, silica, carbon, an alumina compound). The chemical crosslinking or gelating agent can be easily selected by those skilled in the art.

Particularly, as in the case of the aqueous liquid, when providing an environment for treatment or reaction to which a target component-containing sample is subjected, the hydrogel is appropriately prepared by those skilled in the art to have composition suitable for such treatment or reaction.

An example thereof includes a DNA hydrogel (P-gel) that contains polydimethyl siloxane as a base material and can synthesize a protein. This hydrogel is made of DNA as part of a gel scaffold. Such a hydrogel makes it possible, when a target component is a substrate for protein synthesis, to subject a target component to a reaction for obtaining a protein from the target component (a more specific mode can be appropriately determined by those skilled in the art with reference to Nature Materials 8, 432-437 (2009) and Nature Protocols 4: 1759-1770 (2009)). The produced protein can be recovered by, for example, using magnetic particles having an antibody specific to the protein.

[3-2-2. Properties of Gel]

The gel contained in the tube has a property of causing sol-gel transition at a given temperature. The sol-gel transition point may be in the range of 25 to 70° C. Setting the sol-gel transition point to a value in the above range is preferred for a reaction system required to have flowability for recovery etc through solation. The sol-gel transition point may vary depending on conditions such as the type of the organogel material (oil) or hydrogel material, the type of the gelating agent, and the amount of the gelating agent to be added. Therefore, these conditions are appropriately determined by those skilled in the art so that the gel can have a desired sol-gel transition point.

The gel plug is provided on either side of the aqueous liquid contained in the tube so that the aqueous liquid is sandwiched between the gel plugs in the longitudinal direction of the tube, which makes it possible to fix the aqueous liquid in a predetermined position in the tube. On the other hand, magnetic particles can be moved also in the gel by externally manipulating a magnetic field and therefore can pass through the gel. This is due to the thixotropic properties (thixotropy) of the gel. More specifically, the magnetic particles in the tube give a shearing force to the gel along the carrying surface by externally moving a magnet, and therefore the gel located in front of the magnetic particles in a direction, in which the magnetic particles are moved, is fluidized by solation so that the magnetic particles can keep moving forward. Further, after the passage of the magnetic particles, the sol is freed from the shearing force and quickly returned to a gel state, and therefore no through hole is formed in the gel by the passage of the magnetic particles. By utilizing such a phenomenon, a target object can be easily moved using magnetic particles as a carrier, which makes it possible to perform switching among various chemical environments to which the target object is subjected in a very short time. For example, by applying the present invention to a system including two or more chemical reactions using two or more reagents, it is possible to significantly reduce the time required to treat the target object.

By utilizing the property of gelling at ordinary temperature or lower, a reagent showing a liquid state at this temperature can be fixed in the tube by sandwiching the liquid reagent between the gel plugs. Accordingly, this makes it possible to maintain a state where liquid reagents are contained in a capillary in advance from the time of device production to the time when the device reaches a user and therefore to stably supply the liquid reagents. Further, it is possible to eliminate the need for dispensing of a reagent in each process, to reduce effort and time, and further to prevent a reduction in analytical precision due to contamination.

As for the physical properties of the gel, its storage viscoelasticity E', which is one of dynamic viscoelasticity characteristics, may be preferably 10 to 100 kPa, more preferably 20 to 50 kPa at ordinary temperature (20° C.±15° C.). When the storage viscoelasticity is less than the above range, the gel tends to lack strength as a gel plug. When the storage viscoelasticity exceeds the above range, the gel tends to interfere with the movement of magnetic particles even when the magnetic particles have a particle size of about several micrometers.

When the gel is in a sol state, its kinetic viscosity may be 5 $mm^2/s$ to 100 $mm^2/s$, preferably 5 $mm^2/s$ to 50 $mm^2/s$, for example, about 20 $mm^2/s$ (50° C.).

[3-3. Type of Aqueous Liquid]

The aqueous liquid used in the present invention should be insoluble or poorly soluble in the gel, and may be provided as water, an aqueous solution, an emulsion, or a suspension in which microparticles are dispersed. Examples of a constituent of the aqueous liquid include any components that provide an environment for treatment or reaction to which a target component used in the present invention is subjected.

Specific examples of the aqueous liquid include a liquid for liberating a component as a target to be manipulated by the present invention into the aqueous liquid layer to bind or adsorb the component to the surfaces of magnetic particles (i.e., a liquid having the function of separating a target component from a contaminant to promote binding or adsorption of the target component to the surfaces of magnetic beads), a washing liquid for removing a contaminant coexisting with a target component, an eluent for separating a target component adsorbed to magnetic particles from the magnetic particles, and a reaction liquid for constructing a reaction system to which a target component is subjected.

For example, when the target component is nucleic acid, examples of the aqueous liquid include a reagent liquid for disrupting cells to liberate nucleic acid and adsorb the nucleic acid to the surfaces of magnetic particles coated with silica (cell lysis liquid), a washing liquid for washing magnetic particles to remove a component other than nucleic acid, an eluent for separating nucleic acid from magnetic particles (nucleic acid eluent), and a nucleic acid amplification reaction liquid for performing a nucleic acid amplification reaction. Hereinbelow, the above treatment liquids and reaction liquid for nucleic acid and treatments and a reaction to which these liquids are subjected will be described in more detail with reference to a case where the target component is nucleic acid.

[3-3-1. Cell Lysis Liquid]

An example of the cell lysis liquid includes a buffer liquid containing a chaotropic substance. Such a buffer liquid may further contain any chelator such as EDTA or any surfactant such as Triton X-100. The buffer liquid is based on Tris-HCl or any other buffering agent. Examples of the chaotropic substance include guanidinium hydrochloride, guanidinium isocyanate, potassium iodide, and urea.

The chaotropic substance is a strong protein denaturant and therefore has the function of separating a protein such as histone binding to nucleic acid from the nucleic acid to promote adsorption of the nucleic acid to the silica-coated surfaces of magnetic particles. The buffer liquid can be used as an adjuvant that adjusts pH so that nucleic acid can easily adsorb to the surfaces of magnetic particles.

The chaotropic substance also has the function of cell lysis (i.e., cell membrane disruption). However, the surfactant contributes more to cell lysis (i.e., cell membrane disruption) than the chaotropic substance.

The chelator can be used as an adjuvant that promotes cell lysis.

A specific protocol of extraction of nucleic acid from a nucleic acid-containing sample can be appropriately determined by those skilled in the art. In the present invention, magnetic particles are used to transport nucleic acid in a droplet encapsulating medium, and therefore a nucleic acid extraction method is also preferably a method using magnetic particles. For example, extraction of nucleic acid from a nucleic acid-containing sample and purification of the nucleic acid can be performed using magnetic particles by reference to the method described in JP-A-H02-289596.

[3-3-2. Washing Liquid]

The washing liquid is preferably a solution capable of dissolving a component, other than nucleic acid, contained in a nucleic acid-containing sample (e.g., protein, sugar) or another component such as a reagent used for another treatment previously performed, such as nucleic acid extraction, while allowing nucleic acid to remain adsorbed to the surfaces of magnetic particles. Specific examples of the washing liquid include a high-salt aqueous solution of sodium chloride, potassium chloride, or ammonium sulfate and an aqueous alcohol solution such as ethanol or isopropanol.

Washing nucleic acid is to wash magnetic particles having nucleic acid adsorbed thereto. A specific protocol of the washing can also be appropriately determined by those skilled in the art. The number of times of washing of magnetic particles having nucleic acid adsorbed thereto can be appropriately selected by those skilled in the art to the extent that undesired inhibition does not occur during a nucleic acid amplification reaction. From the same viewpoint, when the influence of an inhibitory component can be neglected, the washing step may be omitted.

The number of aqueous liquid layers prepared using the washing liquid is at least the same as the number of times of washing.

[3-3-3. Nucleic Acid Eluent]

As the nucleic acid eluent, water or a buffer liquid containing a salt or the like can be used. Specific examples of the nucleic acid eluent to be used include a Tris buffer liquid, a phosphate buffer liquid, and distilled water.

A specific method for separating nucleic acid from magnetic particles having nucleic acid adsorbed thereto and eluting the nucleic acid into an eluent can also be appropriately determined by those skilled in the art.

[3-3-4. Nucleic Acid Amplification Reaction Liquid]

The nucleic acid amplification reaction liquid used in the present invention contains various elements to be usually used in a nucleic acid amplification reaction, nucleic acid containing at least a base sequence to be amplified, and magnetic particles having the nucleic acid adsorbed to the surfaces thereof.

As will be described later, the nucleic acid amplification reaction is not particularly limited, and therefore the various elements to be used in the nucleic acid amplification reaction can be appropriately determined by those skilled in the art based on, for example, a known nucleic acid amplification method exemplified later. Usually, salts such as $MgCl_2$ and KCl, a primer, deoxyribonucleotides, a nucleic acid synthetase, and a pH buffer liquid are contained. The above salts may be appropriately changed to other salts. There is a case where a substance for reducing non-specific priming, such as dimethylsulfoxide, betaine, or glycerol, is further added.

The nucleic acid amplification reaction liquid used in the present invention may further contain, in addition to the above components, a blocking agent. The blocking agent may be used for the purpose of preventing deactivation of a nucleic acid polymerase caused by adsorption to, for example, the inner wall of a reaction container or the surfaces of magnetic particles.

Specific examples of the blocking agent include proteins such as bovine serum albumin (i.e., BSA), other albumins, gelatin (i.e., denatured collagen), casein, and polylysine, peptides (which may be either natural or synthetic), Ficoll, polyvinylpyrrolidone, and polyethylene glycol.

The nucleic acid amplification reaction according to the present invention is not particularly limited, and may be performed by, for example, a PCR method (U.S. Pat. Nos. 4,683,195, 4,683,202, 4,800,159, and 4,965,188), an LCR method (U.S. Pat. No. 5,494,810), a Qβ method (U.S. Pat. No. 4,786,600), an NASBA method (U.S. Pat. No. 5,409,818), a LAMP method (U.S. Pat. No. 3,313,358), an SDA method (U.S. Pat. No. 5,455,166), an RCA method (U.S. Pat. No. 5,354,688), an ICAN method (Japanese Patent No. 3433929), or a TAS method (Japanese Patent No. 2843586).

Prior to the reaction, an RT reaction may be performed.

The composition of the reaction liquid required for the nucleic acid amplification reaction and the reaction temperature can be appropriately selected by those skilled in the art.

Figure 4:
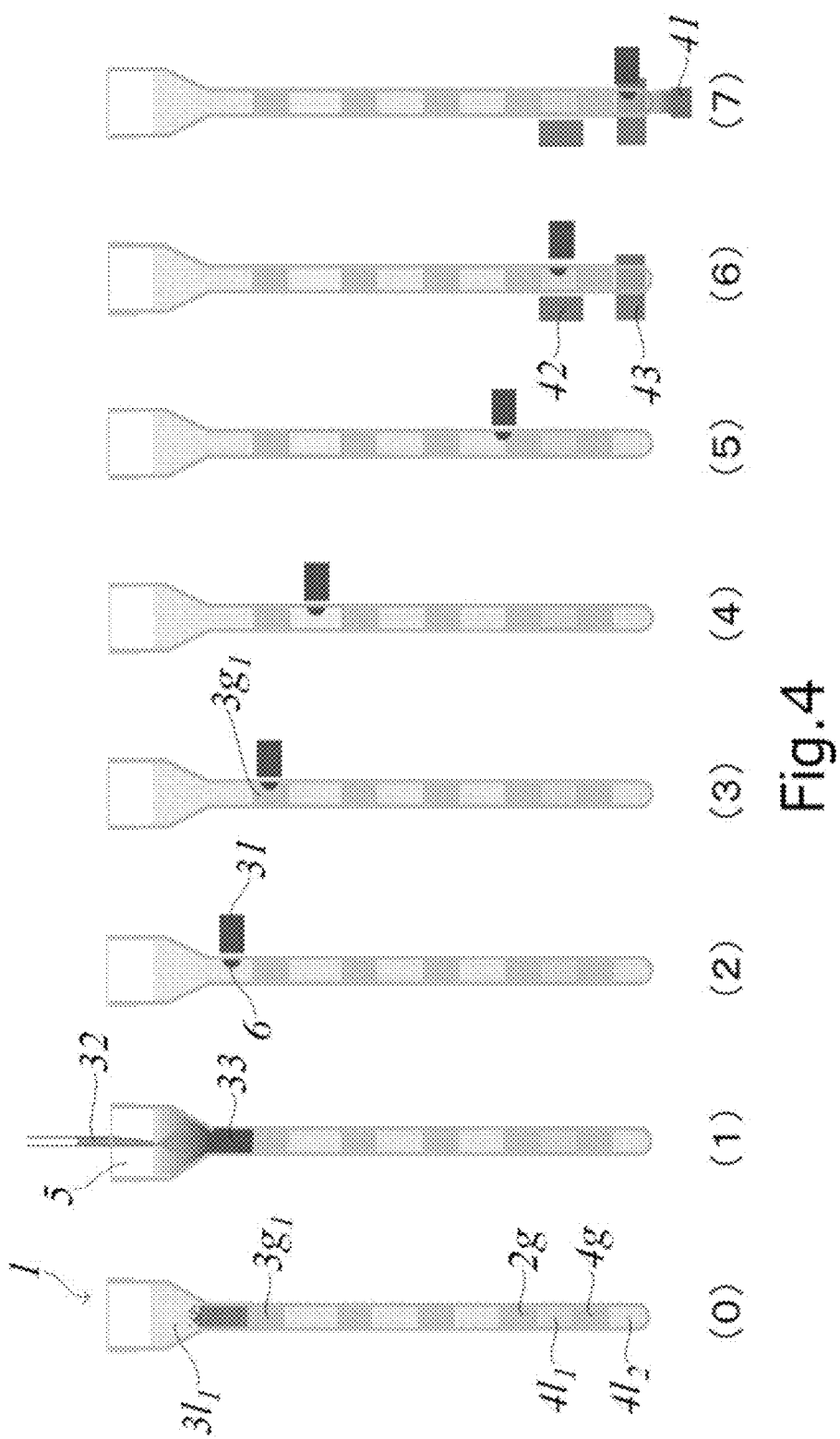
FIG. 4 shows the process of extracting and purifying nucleic acid from a nucleic acid-containing sample, and further performing analysis by reverse transcription reaction and PCR reaction with the use of another example of the manipulation tube according to the present invention.

It is to be noted that when a nucleic acid amplification reaction is further performed after a reverse transcription (RT) reaction, for example, when RT-PCR is performed, a layer composed of an RT reaction liquid may be layered on a layer composed of a PCR reaction liquid with a gel layer interposed therebetween in the recovery part B (see, for example, FIG. 4).

In the case of a real-time nucleic acid amplification method, an amplified product can be fluorescently detected with a fluorescent dye capable of binding to double-stranded DNA or a probe labeled with a fluorescent dye.

Examples of a detection method used in the real-time nucleic acid amplification method are as follows.

For example, when only a target of interest can be amplified by a highly-specific primer, an intercalator method using SYBR (registered trademark) GREEN I or the like is used.

An intercalator that emits fluorescence when binding to double-stranded DNA binds to double-stranded DNA synthesized by a nucleic acid amplification reaction and emits fluorescence having a specific wavelength by irradiation with excitation light. By detecting the fluorescence, the amount of production of an amplified product can be monitored. This method can be used to simply measure various targets without the necessity of designing/synthesizing a fluorescently-labeled probe specific to a target.

When similar sequences need to be distinctively detected or SNPs typing is performed, a fluorescently-labeled probe method is used. An example thereof includes a TaqMan (registered trademark) probe method using, as a probe, an oligonucleotide whose 5' end is modified with a fluorescent substance and 3' end is modified with a quencher substance.

The TaqMan probe is specifically hybridized to template DNA in an annealing step, but emission of fluorescence is suppressed even when the probe is irradiated with excitation light because a quencher is present on the probe. In a step of an elongation reaction, the TaqMan probe hybridized to the template is decomposed by the 5'→3' exonuclease activity of Taq DNA polymerase and the fluorescent dye is liberated from the probe so that the suppression by the quencher is cancelled and fluorescence is emitted. By measuring the intensity of the fluorescence, the amount of production of an amplified product can be monitored.

The principle on which DNA is quantitatively analyzed by real-time PCR using such a method will be described below. First, PCR is performed using, as templates, serially-diluted standard samples with known concentrations. Then, the number of cycles to reach a certain amount of amplified product (threshold cycle: Ct value) is determined. A calibration curve is prepared by plotting the Ct value along the horizontal axis and the initial amount of DNA along the vertical axis.

A sample with an unknown concentration is also subjected to a PCR reaction under the same conditions to determine a Ct value. From this value and the above calibration curve, the amount of DNA of interest contained in the sample can be measured.

Further, in the intercalator method, a melting curve of the amplified product can be obtained by gradually increasing the temperature of a fluorescent dye-containing liquid after PCR reaction from 40° C. to about 95° C. and continuously monitoring the intensity of fluorescence.

Double-stranded DNA produced by a nucleic acid amplification reaction has an inherent Tm value according to the length and base sequence of DNA. That is, by gradually increasing the temperature of a droplet containing DNA bound to a fluorescent dye, the temperature at which the intensity of fluorescence is sharply reduced is observed. The temperature at which the amount of change in the intensity of fluorescence reaches a peak is substantially the same as the Tm value specified by the base sequence and length of DNA. This makes it possible to eliminate data observed by the production of not a gene of interest but, for example, a primer dimer (i.e., false-positive data) from data regarded as positive. In a genetic test, a non-specific reaction often occurs due to contaminants in a sample, and therefore it is important to eliminate such false positives. This also makes it possible to determine whether or not an amplified product produced is inherent in a target gene.

[3-3-5. Other Aqueous Liquids]

The composition of each aqueous liquid used in any reaction or treatment other than the above can also be easily determined by those skilled in the art. Further, even when the target component is a component other than the above nucleic acid, the composition of each aqueous liquid can be easily determined by those skilled in the art.

[4. Method for Producing Manipulation Tube]

As a method for producing the manipulation tube, following two methods are mentioned based on the embodiment of the tube prepared to accommodate multiple layers as a manipulation medium.

[4-1. Case where One Tube is Prepared to Produce One Manipulation Tube]

This production method is applied to a case where the tube is prepared in an integrally-formed state, or a case where the tube is constituted from a manipulation tube portion a and a recovery tube portion b and is prepared in a state where the tube portion a and the tube portion b are connected to each other.

The manipulation tube can be produced by forming a manipulation medium with charging a necessary aqueous liquid and a necessary gel into one tube in a required order from its lower closed end so that the aqueous liquid and the gel are alternately layered.

When the tube is constituted from a manipulation tube portion a and a recovery tube portion b, a recovery part B is first completed at the time when accommodating of a recovery medium necessary for constituting the recovery part B is completed, that is, when accommodating of an aqueous liquid, accommodating of a gel, or formation of multiple layers including an aqueous liquid layer and a gel layer is completed. Further, a manipulation part A is completed by accommodating a manipulation medium necessary for constituting the manipulation part A, that is, by forming multiple layers including an aqueous liquid layer and a gel layer.

A specific method for alternately layering an aqueous liquid and a gel to form multiple layers can be appropriately performed by those skilled in the art according to a layering method that will be described later in 4-2.

It is to be noted that after the completion of housing of a necessary aqueous liquid and/or a necessary gel, the sample supply portion that is an upper open end may be appropriately closed.

[4-2. Case where Two or More Tubes are Prepared to Produce One Manipulation Tube]

This production method is applied to a case where the tube is constituted from a manipulation tube portion a and a recovery tube portion b, and the tube portion a and the tube portion b are prepared in a state where they are independent of each other. In this case, the manipulation tube can be produced by preparing a manipulation part A and a recovery part B separately from each other by accommodating a necessary aqueous liquid and/or a necessary gel into each of the tube portion a and the tube portion b, and then connecting the prepared manipulation part A and the recovery part B to each other.

Figure 2:
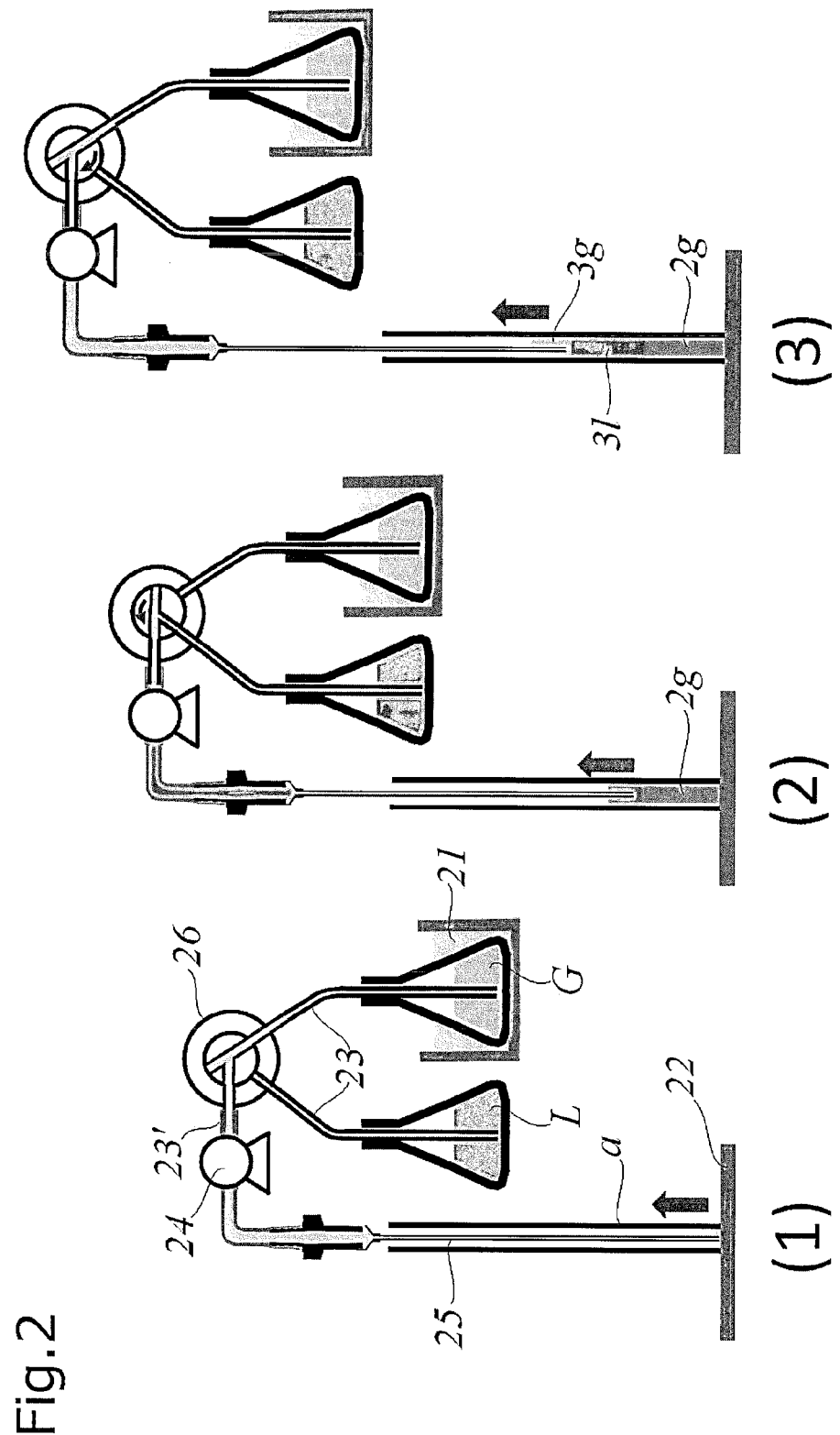
FIG. 2 shows one example of a method for producing the manipulation tube according to the present invention.

The summary of a method for producing the manipulation part A is schematically shown in FIG. 2. An aqueous liquid L (e.g., a washing liquid) for forming an aqueous liquid layer is accommodated in a container and a gel G for forming a gel layer is accommodated in a sol state in another container. In FIG. 2, the gel G is maintained in a sol state by, for example, heating it in a thermostatic bath 21 at 70° C. The tube portion a is prepared in a state where its lower open end is closed by pressing it against a presser mat 22.

A system for sending a liquid into the tube portion a includes tubes 23 each extending from within the container accommodating the aqueous liquid L or the gel G in a sol state to send the aqueous liquid L or the gel G in a sol state, a tube 23', liquid sending means 24 (in FIG. 2, Perista Pump) connected to the tube 23', and a needle 25 for charging a liquid substance sent by the liquid sending means through the tube into the tube portion a. The needle 25 preferably has such a length that when it is inserted into the tube portion a, the tip thereof can reach the bottommost portion of the tube portion a.

In FIG. 2, the tube 23 extending from within the container accommodating the aqueous liquid L and the tube 23 extending from within the container accommodating the gel G in a sol state are connected to a switching valve 26. In this case, by switching the switching valve 26, it is possible to send different liquid substances (aqueous liquid L and gel G in sol state) through the same tube 23' and the same needle 25. Such an embodiment requires only one needle to be inserted into the tube portion a, and is therefore preferred when the tube portion a has a relatively small inner diameter.

On the other hand, all the liquid sending paths extending from within the containers to the needle may be independent of each other without using the switching valve 26. For example, when the same manipulation part A as shown in FIG. 2 is produced, two liquid sending paths can be formed, one of which is formed from a tube extending from within a container accommodating an aqueous liquid and a needle connected to the tube and the other of which is formed from a tube extending from within a container accommodating a gel in a sol state and a needle connected to the tube. Such an embodiment is capable of inserting two needles into the tube portion a, and is therefore preferred when the tube portion a has a relatively large inner diameter.

As shown in FIGS. 2(1) to 2(3) in order, the gel G in a sol state is first charged into the tube portion a, and then the aqueous liquid L and the gel G in a sol state are alternately sent and charged into the tube portion a. The tip of the needle 25 is elevated as the surface level of liquid in the tube portion a is elevated. When the aqueous liquid L is layered on the gel in a sol state as shown in FIG. 2(2) after the gel in a sol state is charged, the gel in a sol state charged before the aqueous liquid L may be completely gelated or may not be completely gelated. A liquid substance sent from the container accommodating the gel G in a sol state into the tube portion a through the needle 25 inserted into the tube portion a is far from the heat source (in FIG. 2, the thermostatic bath 21), and therefore may usually be put into a state intermediate between gel and sol and have increased viscoelasticity. Therefore, even when the layer 2 charged before the aqueous liquid is not completely gelated at the time when the aqueous layer is layered on the layer 2, the gel 2g having a low specific gravity does not float because the contact resistance of the gel 2g acts on the inner wall of the tube portion a.

By alternately sending the gel G in a sol state and the aqueous liquid L into the tube portion a as described above, it is possible to form a necessary number of layers to obtain the manipulation part A.

The recovery part B can be obtained by accommodating a necessary aqueous liquid or gel. Alternatively, the recovery part B may be obtained by appropriately forming multiple layers including an aqueous liquid layer and a gel layer in a required order in the same manner as described above except that the presser mat is not used.

The manipulation part A and the recovery part B obtained as described above are connected to each other. When the manipulation part A is connected to the recovery part B, the tube portion a may be tilted or horizontally placed when separated from the presser mat so that the contents thereof do not slip off. As a mode of the connection, the tube portion a and the tube portion b may be connected to each other by winding a tape or the like, or by providing a connectable joint in each of the tube portion a and the tube portion b and connecting them through the joints.

It is to be noted that after the completion of accommodating of a necessary aqueous liquid and/or a necessary gel, the sample supply portion, which is an upper open end of the manipulation tube portion a, may be appropriately closed. The sample supply portion may be closed after the manipulation part A is produced but before the manipulation part A and the recovery part B are connected to each other or may be closed after the manipulation part A and the recovery part B are connected to each other.

[5. Magnetic Particles]

The magnetic particles are used to move a target component together with a small amount of liquid lump in the manipulation tube by varying a magnetic field from the outside of the manipulation tube. The magnetic particles intended to make it possible to separate, recover, and purify a specific component by such movement usually have a chemical functional group on their surface. The magnetic particles may not be accommodated in the manipulation tube in advance (FIGS. 1(1) and 1(2)), or may be accommodated in the manipulation tube in advance (FIGS. 1(3), 3, and 4). When accommodated in the manipulation tube in advance, the magnetic particles may be contained in the aqueous liquid constituting the uppermost layer. When not accommodated in the manipulation tube in advance, the magnetic particles are supplied into the manipulation tube at the time when a target component-containing sample is supplied into the manipulation tube.

The magnetic particles are not particularly limited as long as they are particles that respond to magnetism. Examples thereof include particles having a magnetic material such as magnetite, γ-iron oxide, or manganese zinc ferrite. Further, the magnetic particles may have a surface having a chemical structure specifically binding to a target component to be subjected to the above-described treatment or reaction, such as an amino group, a carboxyl group, an epoxy group, avidin, biotin, digoxigenin, protein A, protein G, a complexed metal ion, or an antibody or may have a surface specifically binding to a target component by electrostatic force or van der Waals force. This makes it possible to selectively adsorb a target component to be subjected to reaction or treatment to the magnetic particles.

Examples of a hydrophilic group on the surface of the magnetic particles include a hydroxyl group, an amino group, a carboxyl group, a phosphoric group, and a sulfonic group.

The magnetic particles may further contain, in addition to the above elements, various elements appropriately selected by those skilled in the art. Preferred specific modes of the magnetic particles having a hydrophilic group on their surface include particles composed of a mixture of a magnetic material and silica and/or an anion exchange resin, magnetic particles whose surfaces are coated with silica and/or an anion exchange resin, magnetic particles whose surfaces are coated with gold having a hydrophilic group binding thereto through a mercapto group, and gold particles containing a magnetic material and having a hydrophilic group binding to their surface through a mercapto group.

The average particle size of the magnetic particles having a hydrophilic group on their surface may be about 0.1 µm to 500 µm. When the average particle size is small, the magnetic particles are likely to be present in a dispersed state in the aqueous liquid layer when freed from a magnetic field.

Examples of the magnetic particles commercially available include silica-coated Magnetic Beads for nucleic acid extraction, which are a constituent reagent for Plasmid DNA Purification Kit MagExtractor-Plasmid—available from Toyobo CO., Ltd. In such a case where magnetic particles are sold as a constituent reagent for a kit, a raw liquid product containing magnetic particles contains a preservative liquid or the like, and therefore the magnetic particles are preferably suspended in pure water (e.g., in about ten times amount of pure water) to wash them. Such washing can be performed by suspending the magnetic particles in pure water and then removing a supernatant by centrifugation or by agglomerating the magnetic particles together using a magnet. The suspension and the supernatant removal may be repeatedly performed.

It is to be noted that the magnetic field applying means to vary a magnetic field to move the magnetic particles will be described later in detail in Section 8.

[6. Method for Manipulating Target Component in Tube]

Figure 3:
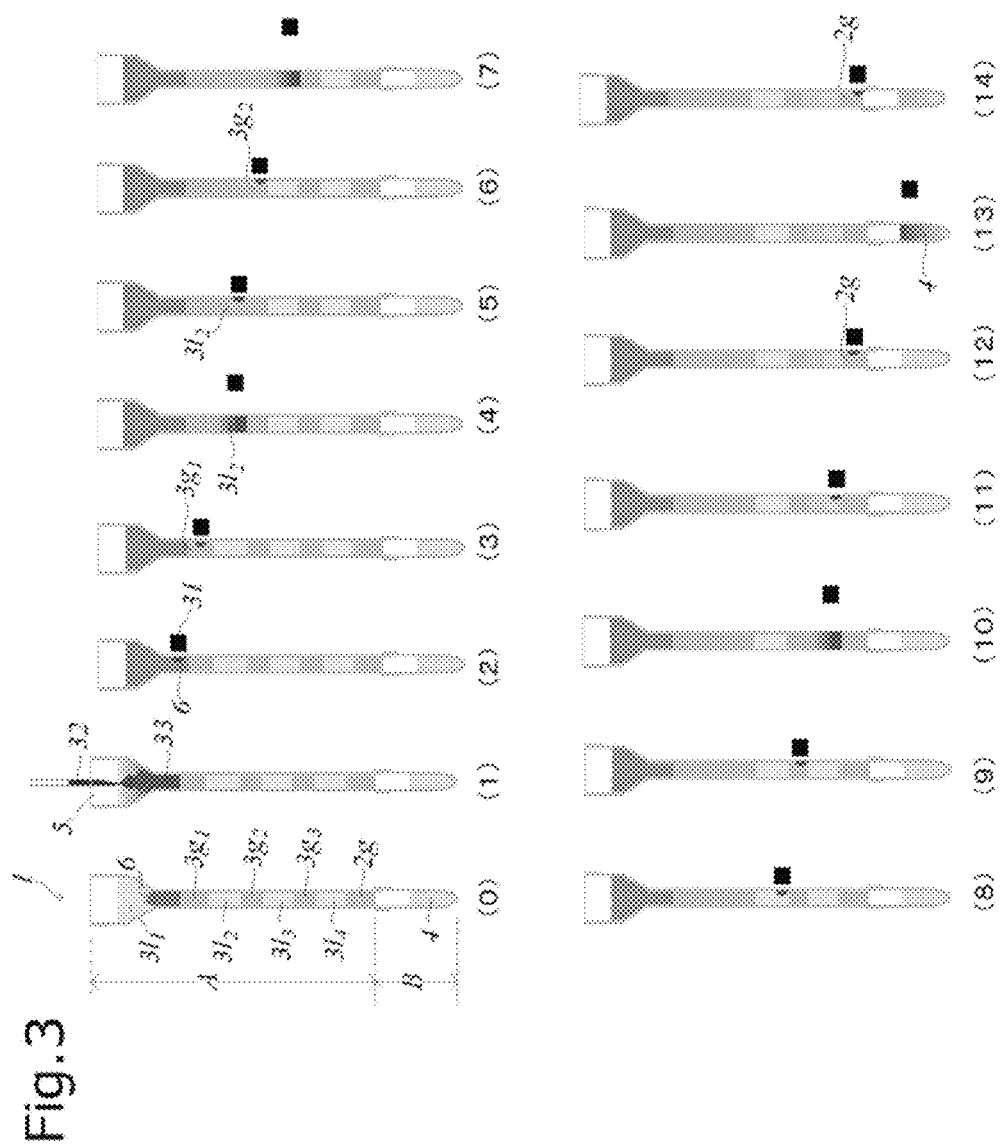
FIG. 3 shows the process of extracting and purifying nucleic acid from a nucleic acid-containing sample with the use of the manipulation tube according to the present invention shown in FIG. 1(3).

The manipulation of a target component in a manipulation tube is shown in FIGS. 3(0) to 3(14) and FIGS. 4(0) to 4(7). Hereinbelow, a description will be made with reference to FIGS. 3 and 4.

[6-1. Supply of Sample into Manipulation Tube]

When a manipulation tube is used, a sample 32 containing a target component is supplied through a sample supply port 5 (FIG. 3(1) and FIG. 4(1)). Usually, the sample is supplied in a liquid form. The sample supply may be performed manually using a syringe or the like or may be performed under automatic control by a dispenser using a pipetter or the like. The sample supply may be performed in a state where the manipulation tube is placed in a standing position with the use of appropriate holding means (not shown; it is to be noted that means for holding the manipulation tube will be described later in detail in Section 7).

In an uppermost layer in the manipulation tube, an aqueous liquid mixture 33 containing the target component-containing sample 32, magnetic particles 6, and an aqueous liquid $31_1$ is obtained. More specifically, such an aqueous liquid mixture can be obtained by the following manner.

For example, when the uppermost layer accommodated in the manipulation tube is composed of the aqueous liquid, the sample may be supplied into the manipulation tube together with the magnetic particles, or may be supplied into the manipulation tube together with the aqueous liquid and the suspended magnetic particles. This makes it possible to obtain an aqueous liquid mixture from the aqueous liquid in the uppermost layer.

Further, for example, when the uppermost layer accommodated in the manipulation tube is composed of the aqueous liquid containing the magnetic particles (which corresponds to a case shown in FIGS. 3 and 4), only the sample may be supplied into the manipulation tube or the sample may be supplied into the manipulation tube together with the aqueous liquid. This makes it possible to obtain an aqueous liquid mixture from the aqueous liquid containing the magnetic particles in the uppermost layer.

Further, for example, when the uppermost layer accommodated in the manipulation tube is composed of a gel, the sample may be supplied into the manipulation tube together with the aqueous liquid and the magnetic particles. This makes it possible to form an aqueous liquid mixture as a new uppermost layer on the gel layer.

[6-2. Manipulation in Manipulation Tube]

The manipulation tube in which the aqueous liquid mixture containing the sample and the magnetic particles has been prepared in the uppermost layer by supplying the sample can be set in a device in a state where the manipulation tube remains standing in the holding means or the manipulation tube is transferred to dedicated holding means in the device. In the device, a magnetic field is produced by bringing magnetic field applying means 31 (e.g., a cylindrical neodymium magnet having a diameter of 1 mm to 5 mm and a length of 5 mm to 30 mm) close to a manipulation tube 1 on the outside of the manipulation tube 1 to agglomerate the magnetic particles 6 dispersed in the aqueous liquid mixture layer 31$_1$ together with the target component (FIG. 3(2) and FIG. 4(2)). At this time, an unnecessary component contained in the aqueous liquid mixture layer 31$_1$ may also be agglomerated together. By moving the magnetic field applying means 31 downward at a rate of 0.5 to 10 mm/second, the magnetic particles accompanied by the target component are transported from the aqueous liquid mixture layer 31$_1$ through a gel layer 3g$_1$ that is in contact with and located directly below the aqueous liquid mixture layer 31$_1$ (FIG. 3(3) and FIG. 4(3)) to an aqueous liquid layer 31$_2$ that is in contact with and located directly below the gel layer 3g$_1$ (FIG. 3(4) and FIG. 4(4)). It is to be noted that the magnetic particles passing through the gel layer 3g$_1$ are thinly coated with the aqueous liquid mixture of the aqueous liquid mixture layer 31$_1$, to which the magnetic particles are exposed before passing through the gel layer 3g$_1$, and are therefore accompanied by not only the target component but also a contaminant component, although the concentration of the contaminant component has been reduced. Such magnetic particles are further transported to the aqueous liquid layer 31$_2$.

The size and moving rate of the magnet are appropriately determined by those skilled in the art based on the amount of the magnetic particles, the inner and outer diameters of the manipulation tube, the conditions of the gel plug, and the like.

Further, transport of the magnetic particles by the magnetic field applying means 31 from the aqueous liquid layer 31$_2$ through a gel layer to another aqueous liquid layer is repeatedly performed, if necessary. The "repeatedly performed, if necessary" means that transport manipulation may be repeated as many times as the number of layers by moving the magnetic particles only in one direction from top to bottom in principle (FIGS. 3(4) to 3(13) and FIGS. 4(4) to 4(7)) or transport manipulation may be repeated a number of times equal to or larger than the number of layers not only by moving the magnetic particles only in one direction from top to bottom but also by moving back the magnetic particles in a direction from bottom to top appropriately. That is, another aqueous liquid layer into which the magnetic particles are to be transported may be present above or below the aqueous liquid layer from which the magnetic particles are transported.

By repeating such transport manipulation, the amount of the contaminant component transported by the magnetic particles together with the target component approaches zero as much as possible. The magnetic particles are accompanied not only by the target component but also by a very small amount of washing liquid, but the target component on the surfaces of the magnetic particles is purified to such a level that a subsequent analysis step or the like is not affected. In this way, the target component can be very efficiently purified only by magnetic field manipulation.

In the aqueous liquid layer, the magnetic particles accompanied by the target component (more specifically, in the case of the target component accompanied by an unnecessary component or in the case of the target component from which an unnecessary component has been removed) are preferably manipulated to be able to sufficiently come into contact with the aqueous liquid from the viewpoint of improving treatment efficiency. An example of a method for efficiently performing such manipulation includes a method in which the magnetic field applying means is moved upward and downward in a state where the magnetic particles are agglomerated together by the application of a magnetic field in the aqueous liquid layer. Another example of the method is a method in which the magnetic particles, to which a magnetic field is applied by the magnetic particles, are freed from the magnetic field to naturally disperse the magnetic particles agglomerated together by magnetic field application.

A specific example of such a method is as follows. As shown in FIG. 3(4), a magnetic field is once blocked or reduced by keeping the magnetic field applying means 31 away from the manipulation tube 1 to disperse the magnetic particles in the washing liquid layer 31$_2$. This allows the target component adsorbed to the magnetic particles and an accompanying component to be washed by sufficient exposure to the washing liquid 31$_2$. As shown in FIG. 3(5), the magnetic particles are agglomerated together with the target component by again bringing the magnetic field applying means 31 close to the manipulation tube 1 so that the magnetic particles are put into a state where they can be transported. Further, as shown in FIG. 3(6), by moving the magnetic field applying means 31 downward, the magnetic particles are also transported to a gel layer 3g$_2$ located directly below the washing liquid layer 31$_2$. The amount of the accompanying component transported by the magnetic particles together with the target component into the gel layer 3g$_2$ shown in FIG. 3(6) is smaller than that of the accompanying component transported by the magnetic particles together with the target component into the gel layer 3g$_1$ shown in FIG. 3(3) because the accompanying component is partly or mostly removed by washing as shown in FIG. 3(4).

After the target substance is separated from the magnetic particles in a layer accommodated in a recovery part B, the target substance can be recovered in the recovery part in a state where it is eluted from the magnetic particles by moving the magnetic particles, from which the target substance has been separated, from the layer in which the separation of the target substance has been performed to another layer (e.g., FIGS. 3(13) and 3(14)).

[6-3. Nucleic Acid Extraction]

For example, when the surfaces of the magnetic particles are coated with silica, as shown in FIG. 3, a biological sample is subjected to a cell lysis liquid 31$_1$ containing a surfactant and a chaotropic salt such as guanidinium thiocyanate to liberate nucleic acid from cells (FIG. 3(1)). The liberated nucleic acid can be specifically adsorbed to the silica surfaces of the particles. The adsorbed nucleic acid is accompanied by a reaction inhibiting-component in this state and therefore cannot be directly used as a template for gene amplification reaction. Accordingly, the magnetic particles are washed with a washing liquid $31_2$ while having the nucleic acid adsorbed to the surfaces thereof. At this time, the magnetic particles 6 are collected by the magnet 31 (FIG. 3(2)) and passed through a gel plug $3g_1$ separating the cell lysis liquid $31_1$ and the washing liquid $31_2$ (FIG. 3(3)) so that a large amount of the reaction-inhibiting component is not brought into the washing liquid. By allowing the magnetic particles to pass through the gel plug $3g_1$, the magnetic particles can reach the washing liquid $31_2$ with little liquid fraction (FIG. 3(4)). This makes it possible to wash the magnetic particles with high efficiency. By further repeatedly performing passage of the magnetic particles through a gel plug ($3g_2$, $3g_3$) and transport of the magnetic particles into a washing liquid ($31_3$, $31_4$) (FIGS. 3(5) to 3(10)), the degree of purification of the nucleic acid can be increased. The nucleic acid purified in a state where it is adsorbed to the surfaces of the magnetic particles is again collected by the magnet (FIG. 2(11)), passed through a gel plug 2g (FIG. 3(12)), and transported into an eluent 4 (FIG. 3(13)). In the eluent 4, the nucleic acid is separated from the magnetic particles and eluted into the eluent. When the mixing of the magnetic particles into the eluent is not desirable, the magnetic particles from which the nucleic acid has been eluted are again held in the gel plug 2g so that the purified nucleic acid eluted from the magnetic particles remains in the recovery part B (FIG. 3(14)). The thus obtained nucleic acid is useful as template nucleic acid that can be analyzed by a nucleic acid amplification reaction. The obtained nucleic acid can be subjected to next manipulation (step of performing analysis by nucleic acid amplification reaction) by detaching the recovery part B of the manipulation tube from the manipulation part A.

[6-4. Nucleic Acid Synthesis/Analysis]

As shown in FIG. 4, when the manipulation tube to be used is obtained by integrally forming the tube portion a of the manipulation part A and the tube portion b of the recovery part B and has the same manipulation part A as shown in FIG. 3 and the recovery part B accommodating an RT reaction liquid $41_1$ and a PCR reaction liquid $41_2$ separated by a gel plug 4g, the same manipulations as shown in FIGS. 3(1) to 3(12) are performed (FIGS. 4(1) to 4(5)), and then the magnetic particles 6 are transported into the RT reaction liquid $41_1$ with purified nucleic acid (RNA) being adsorbed thereto to perform an RT reaction (FIG. 4(7)). After the completion of the RT reaction, the magnetic particles adsorb also DNA (which is used as a template for PCR reaction) obtained by the RT reaction, pass through the gel plug 4g, and are transported into the PCR reaction liquid $41_2$ to perform a PCR reaction (FIG. 4(7)). A PCR product can be analyzed by a fluorescent detection method using a fluorescent dye such as a real-time detection method or an end-point detection method.

It is to be noted that in FIG. 4, reference signs 42 and 43 schematically indicate a temperature control function. A specific example of the temperature control function 42 will be described later in Section 8-2-6 and a specific example of the temperature control function 43 will be described later in Section 7-3.

Figure 5:
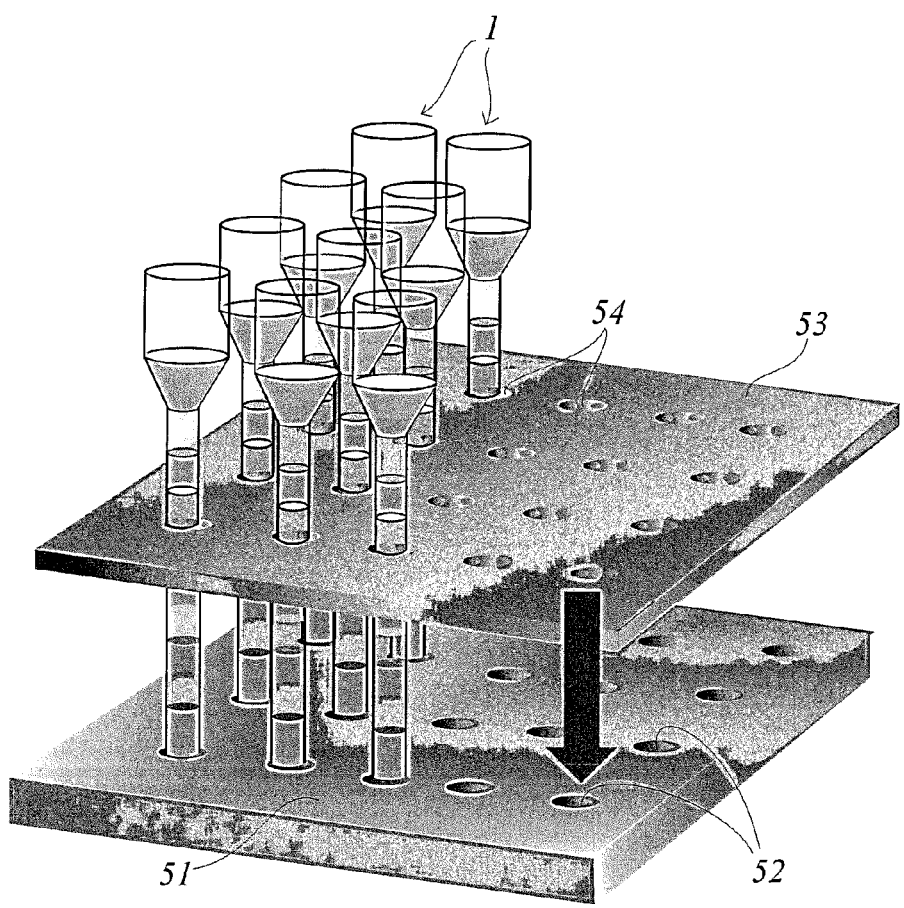
FIG. 5 is a perspective view showing one example of a device multi-channeled using the two or more manipulation tubes according to the present invention to be able to simultaneously perform manipulations in the manipulation tubes.

When the above manipulations are simultaneously performed in the two or more manipulation tubes, as shown in FIG. 5, the device can be multi-channeled. The device illustrated in FIG. 5 has a simple structure including, as main units, magnetic field applying means (movable magnetic plate 53) having a magnet-moving system and a holding substrate with temperature control function (temperature adjustment block 51). The structures of these units will be described later in Section 7 and Section 8.

[6-5. Synthesis, Separation and Analysis of Protein]

[6-5-1. Protein Synthesis Using Hydrogel (P-Gel)]

A cell-free protein synthesis system using polydimethyl siloxane as a base material is disclosed in the above reference document (Nature materials 8, 432-437 2009). The cell-free protein synthesis system is performed in a general-purpose sample tube, but such a cell-free protein synthesis system can be constructed also in the manipulation tube according to the present invention.

[6-5-2. Analysis Utilizing Interaction Between Protein of Interest and Another Protein]

Commercially-available purification kits already exist as means for separating/recovering a protein by utilizing an antigen-antibody reaction between the protein and an antibody (which is also a protein) produced against the protein. They are performed by a protocol using a general-purpose tube and a centrifuge. Also in the above cell-free protein synthesis system, a synthesized protein is separated using a spin column prepared separately from the sample tube.

In the present invention, the use of magnetic particles having an antibody against a protein of interest immobilized on the surfaces thereof makes it possible to separate and obtain the protein of interest in one manipulation tube without moving the protein of interest between different devices.

[6-5-3. Mass Analysis of Protein Adsorbed to Magnetic Particles]

A technique is disclosed in a reference document (Analytical Chemistry, 77, 5912-5919, 2005) and the like, in which magnetic particles whose surfaces are coated with titanium oxide are prepared, and a separately-prepared protein to be subjected to mass spectrometry is adsorbed to the magnetic particles, directly mixed with a matrix, and analyzed by a mass spectrometer. In the present invention, preparation of a protein to be subjected to mass spectrometry and adsorption of the protein to magnetic particles can be performed in one manipulation tube.

[7. Holding Means]

The manipulation tube is usually set substantially vertically (i.e., in a standing position) so that the sample supply portion, which is an opening, faces upward during use. The manipulation tube can be set using appropriate holding means. The same holding means or different holding means may be used during sample supply and target component manipulation. When different holding means are used during sample supply and target component manipulation, transfer of the manipulation tube between the holding means may be performed either manually or automatically.

[7-1. Holding Mode]

The holding means is not particularly limited as long as it can usually hold the manipulation tube substantially vertically (i.e., in a standing position) so that the sample supply portion, which is an opening, faces upward. For example, holding members each having a holding hole, into which the closed end portion of the manipulation tube can be inserted to hold the manipulation tube, may be used singly or in combination of two or more of them, or a rack formed by arranging linear members in a reticular pattern so that a lattice hole is formed as a holding hole may be used, but the holding means is not limited thereto. In the former case, the holding hole formed in the holding member may be either a through hole or a blind hole. The inner diameter of the holding hold is determined based on the outer diameter of the manipulation tube to be held.

The holding member that holds the closed end portion of the manipulation tube is referred to as a holding substrate. The holding hole in the holding substrate may be formed so that the closed end of the holding part B does not penetrate through the holding substrate (i.e., so that the holding hole itself does not penetrate through the holding substrate). The depth of the holding hole is appropriately determined based on the range of the manipulation tube desired to be held.

[7-2. Holding of Two or More Manipulation Tubes]

The manipulation tube according to the present invention is long and thin and has a very small installation area when placed in a standing position, and therefore two or more manipulation tubes can be densely packed in a standing position even in a small installation area. This makes it possible to simultaneously manipulate the manipulation tubes. That is, manipulation can be multi-channeled.

One example of this mode is shown in FIG. 5. A device shown in FIG. 5 can treat simultaneously up to 20 manipulation tubes. Of course, a larger number of manipulation tubes can be treated depending on the specifications of the device. For example, when there is a space similar in size to a standard 96-well plate, up to 96 manipulation tubes can be placed in a standing position, which makes it possible to treat simultaneously up to 96 samples. Further, the manipulation tubes are independent of each other, and therefore in the above example, the number of the manipulation tubes can be arbitrarily increased or decreased depending on the number of samples. Such a mode is particularly useful for POCT (Point Of Care Testing) in which the number of samples is small and variable.

When two or more manipulation tubes are placed in a standing position, for example, as shown by a reference sign 51 in FIG. 5, the holding substrate may have two or more holding holes 52. The pattern of the holding holes varies depending on a mode where the manipulation tubes are densely packed. For example, the holding holes may be formed in an array (i.e., in line one-dimensionally) or, as shown in FIG. 5, in a matrix (i.e., two-dimensionally). The distance between the adjacent holding holes 52 can be appropriately determined based on the density of the manipulation tubes. Further, when the manipulation tube held in the holding hole 52 has a larger inner diameter at its sample supply portion, the distance between the adjacent holding holes 52 can be appropriately determined based on the outer diameter of the sample supply portion.

[7-3. Temperature Control Function]

The holding means may have a temperature control function. More specifically, the holding means may have a temperature control function in its portion that holds at least part of the recovery part B. For example, the temperature control function is schematically shown by a reference sign 43 in FIG. 4. More specifically, when the holding substrate holds the closed end portion of the recovery part B in its holding hole, its holding portion may have a temperature control function. For example, the holding substrate 51 itself shown in FIG. 5, which is designed to hold the closed end portion of the recovery part B in the holding hole 52, may be constituted from a temperature adjustment block. The temperature control function makes it possible to perform treatment or reaction requiring temperature control in the aqueous liquid accommodated in at least the lower end of the recovery part B. In the present invention, this mode is preferably used, for example, when a nucleic acid amplification reaction is performed in the recovery part B.

[7-4. Optical Detection Port]

Figure 7:
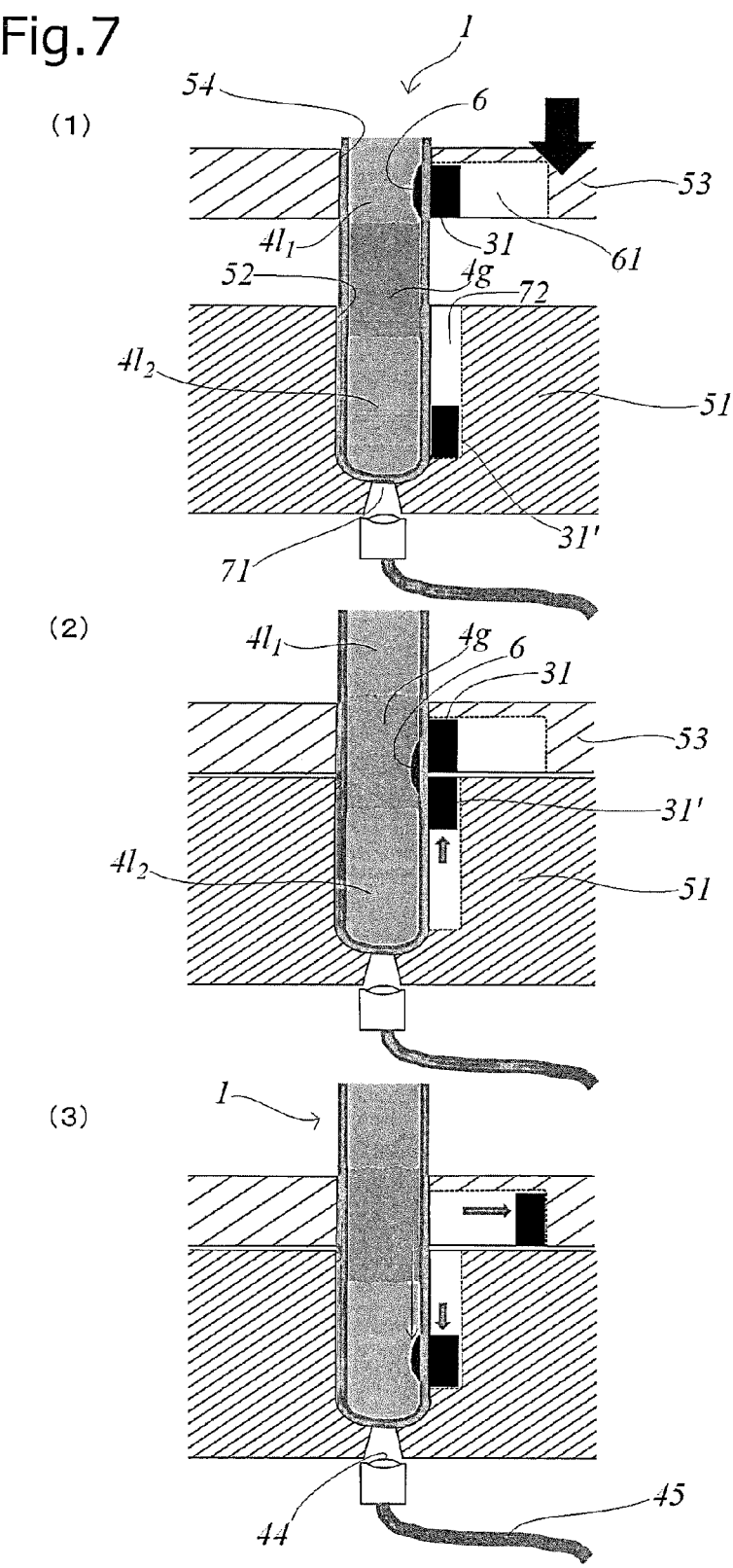
FIG. 7 is a longitudinal sectional view of a portion including an modified example of the magnetic field applying means (movable magnetic plate) shown in FIG. 5, a modified example of holding means (holding substrate) shown in FIG. 5, and a manipulation tube held by the holding means.

The holding substrate may further have an optical detection port. The optical detection port is provided to irradiate the inside of the recovery part B with excitation light to detect a signal that is emitted during treatment or reaction performed in the recovery part B and is derived from a target component or a component related thereto. For example, as shown in FIG. 7, an optical detection port 71 may be formed at the lower end of the holding hole 52 to penetrate through the holding substrate and have a diameter smaller than the outer diameter of the tube portion b held in the holding hole 52. The optical detection port 71 may be provided with optical detection means (in FIG. 7, a fluorescence detection lens 44 and an optical fiber cable 45 are included). The position of the optical detection port is not limited to that shown in FIG. 7 and may be determined in consideration of, for example, optical measurement from the side surface of the recovery part.

[8. Magnetic Field Applying Means]

The magnetic field applying means and its magnetic field moving system which causes variations in a magnetic field to move magnetic particles in the manipulation tube together with a target component are not particularly limited. As the magnetic field applying means, a magnetic source such as a permanent magnet (e.g., ferrite magnet, neodymium magnet) or an electromagnet can be used. The magnetic field applying means can be provided outside of and close to the manipulation tube to the extent that magnetic particles, which are dispersed in the aqueous liquid layer in the manipulation tube, are agglomerated together on the carrying surface side of the tube and the magnetic particles agglomerated together in the gel layer in the manipulation tube can be transported. This makes it possible to allow the magnetic field applying means to effectively produce a magnetic field for magnetic particles with the carrying surface of the tube interposed therebetween to capture and transport a target component together with the agglomerated magnetic particles.

[8-1. Shape]

The shape of the magnetic field applying means is not particularly limited. For example, a block object (e.g., the magnet 31 illustrated in FIG. 3 or 4) that can produce a magnetic field at a point or in part of the manipulation tube may be used. More specifically, the magnetic field applying means may have a cylindrical shape (with a diameter of, for example, 1 mm to 5 mm and a thickness of, for example, 5 mm to 30 mm). When the magnetic field applying means has such a shape, a magnetic field can be produced in the manipulation tube by placing the magnetic field applying means at a point or in part of the outer periphery of the manipulation tube. On the other hand, the magnetic field applying means may be a ring-shaped magnet that has a substantially circular hole in its center and can produce a magnetic field around the manipulation tube having a substantially circular cross-section. When the magnetic field applying means has such a shape, a magnetic field can be produced in the manipulation tube by passing the manipulating tube through the substantially circular hole provided in the center of ring of the magnetic field applying means. In this case, the magnetic field applying means having a ring shape surrounds the manipulation tube, and therefore magnetic particles also form a ring shape according to the shape of the magnetic field applying means when agglomerated together. On the other hand, when the magnetic field applying means has a block shape, magnetic particles also form a block shape when agglomerated together. That is, the use of the magnetic field applying means having a ring shape is preferred in that the contact area between magnetic particles and an aqueous liquid is larger, and therefore a target component adsorbed to the magnetic particles and the like can be more efficiently exposed to a liquid constituting the aqueous liquid layer.

[8-2. Magnetic Field Moving System]

[8-2-1. Movement in Longitudinal Direction of Manipulation Tube]

The magnetic field moving system of the magnetic field applying means may be, for example, a system that can move a magnetic field in the longitudinal direction (axial direction, at least downward direction) of the manipulation tube in a state where magnetic particles can remain agglomerated together. In the following description, the magnetic field moving system refers to a system that can determine a stopping position and can control a moving rate manually or automatically using a computer or the like. The moving rate may be, for example, 0.5 to 10 mm/second.

The magnetic field moving system is preferably a system that can physically move the magnetic field applying means itself in the longitudinal direction of the manipulation tube. The magnetic field moving system can vertically move the magnetic field applying means (permanent magnet 31 in FIG. 3 or 4) itself as shown in FIG. 3 or 4. Further, also in the case of the device, as shown in FIG. 5, in which two or more manipulation tubes are densely packed, the magnetic field applying means (movable magnetic plate 53 in FIG. 5) can be vertically moved (in either case, the magnetic field moving system itself is not shown).

[8-2-2. Control of Strength of Magnetic Field]

The magnetic field moving system of the magnetic field applying means may be a system that can variably control the strength of a magnetic field to be applied to magnetic particles. More specifically, the magnetic field may be blocked or reduced. The magnetic field is preferably blocked or reduced to the extent that agglomerated magnetic particles can be dispersed in a droplet (see the above Section 6-2).

For example, in the case of an electromagnet, a magnetic field can be blocked using means for controlling the application of electric current.

For example, in the case of a permanent magnet, a system can be used which can keep the magnet placed outside the manipulation tube away from the manipulation tube. This system may be controlled either manually or automatically. Magnetic particles can be naturally dispersed in the aqueous liquid layer by reducing a magnetic field applied to the magnetic particles, preferably by releasing the magnetic particles from a magnetic field. This makes it possible to sufficiently expose a target component or an accompanying component adsorbed to the magnetic particles to a liquid constituting the aqueous liquid layer.

[8-2-3. Case of Device in which Two or More Manipulation Tubes are Closely Packed]

Figure 6:
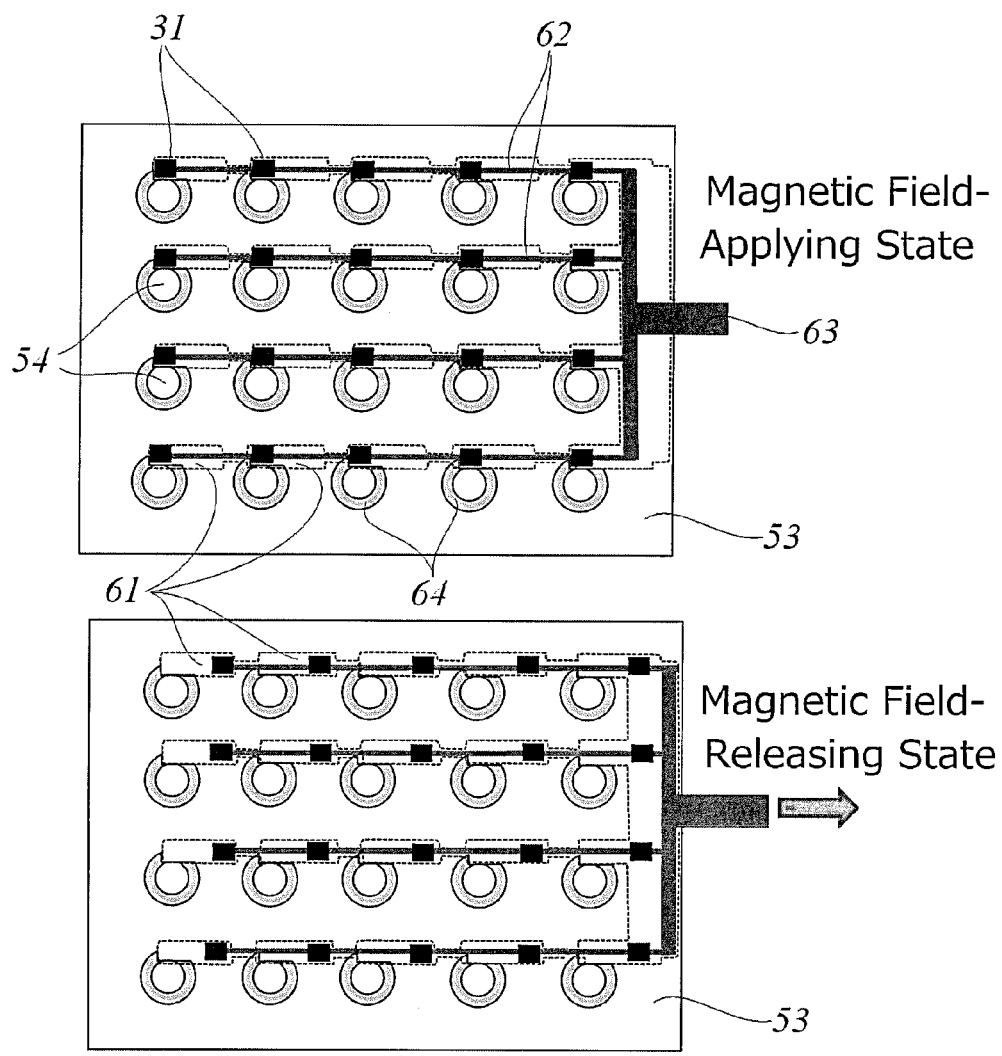
FIG. 6 is across sectional view of a modified example of magnetic field applying means (movable magnetic plate) shown in FIG. 5.

As shown in FIG. 5, the device in which two or more of the manipulation tubes 1 are densely packed can hold two or more magnetic sources corresponding to the manipulation tubes by unitizing them into one member that can be moved in the longitudinal direction of the manipulation tube. As shown in FIG. 5, such a unitized member may be embodied as the movable magnetic plate 53 that is magnetic field applying means movable in the longitudinal direction of the manipulation tube 1. As shown in FIG. 6, the movable magnetic plate 53 shown in FIG. 5 includes a movable substrate that can be moved in the longitudinal direction of the manipulation tube and magnetic sources (magnets 31) held in the movable substrate, and the magnets 31 may be held in a state where they are arranged to correspond to the manipulation tubes, respectively.

Further, the above member may have the function of holding the manipulation tubes like the above-described holding means or may not have such a function. In the case shown in FIG. 5, the movable magnetic plate 53 is allowed to have a holding function by forming holding holes 54 corresponding to the manipulation tubes 1.

It is to be noted that in FIG. 6, the magnetic field applying means has a block shape, but may have a ring shape having a hollow corresponding to the holding hole 54.

As shown in FIG. 5, in the device in which two or more of the manipulation tubes 1 are densely packed, the magnetic field moving system of the magnetic field applying means may be a system that can simultaneously perform the control of strength of a magnetic field applied by the magnetic field applying means on the manipulation tubes. For example, when two or more different magnetic field applying means are used for the manipulation tubes, respectively, the magnetic field moving system may be a system that can simultaneously control magnetic fields produced by two or more of the magnetic field applying means.

When an electromagnet is used as the magnetic field applying means in the above member, a magnetic field can be controlled by electric current control.

On the other hand, when a permanent magnet is used as the magnetic field applying means, the above member can have, for example, a system that moves the member itself closer to or away from the manipulation tubes (e.g., moves the member itself substantially perpendicular to the longitudinal direction of the manipulation tube), or inserts a magnetic shielding material between the magnetic field applying means and each of the manipulation tubes, or moves two or more of the magnetic field applying means held in the member closer to or away from the manipulation tubes at a time without moving the member itself.

As shown in FIG. 6, in the movable magnetic plate 53 shown in FIG. 5, the magnets 31 respectively corresponding to the manipulation tubes held in the holding holes 54 may be arranged in a state where each of the magnets 31 is housed in a magnet holding portion 61. The magnet holding portion 61 is formed to have a size that allows the magnet 31 to move in the movable magnetic plate 53 (i.e., magnet 31 being moved closer to or away from the manipulation tube). As shown in FIG. 6, the magnets 31 are connected to each other by connecting bars 62 and all the connecting bars 62 can be connected to a handle member 63. By handling the handle member 63, as shown in FIG. 6, all the magnets can be moved closer to the manipulation tubes (i.e., a state where magnetic fields are applied to the manipulation tubes), or away from the manipulation tubes (i.e., a state where the manipulation tubes are released from magnetic fields).

It is to be noted that when a magnet having a ring shape is used to control the strength of a magnetic field, the ring-shaped magnet may be, for example, a magnet constituted from two or more arc-shaped magnetic parts to form a ring shape. Such a ring-shaped magnet can be divided in a direction substantially perpendicular to the diametrical direction thereof to free the manipulation tube from a magnetic field.

[8-2-4. Movement of Magnetic Field Applying Means in Holding Means that can Hold Recovery Part B]

The holding means can have a recess that allows the magnetic field applying means to move in the longitudinal direction of the tube portion b. More specifically, the holding means can have, in a portion that holds the recovery part B, a recess that allows the magnetic field applying means to move in the longitudinal direction of the tube portion b. The magnetic field applying means that moves in the recess may be the same as or different from the magnetic field applying means that has contributed to manipulations performed in the manipulation part A. For example, as shown in FIG. 7(1), a recess 72 is formed in the holding substrate 51 (in FIG. 7, the holding substrate 51 is constituted from a temperature adjustment block) having the holding hole 52, and a magnet 31' is previously accommodated in the recess. The movable magnetic plate 53 having the magnet 31 arranged therein is moved downward, and as shown in FIG. 7(2), the movable magnetic plate 53 is put into a state where it comes into contact with the holding substrate 51 and therefore cannot be moved downward anymore. That is, the magnet 31 cannot move the magnetic particles 6 downward anymore. At this time, the magnet 31' accommodated in the recess 72 of the holding substrate 51 is attracted to the magnet 31 by a magnetic field produced by the magnet 31 in the movable magnetic plate 53. Then, the magnetic particles 6 in the manipulation tube 1 are attracted to both the magnet 31 and the magnet 31'. Then, as shown in FIG. 7(3), the magnet 31' is freed from the magnetic field produced by the magnet 31 by keeping the magnet 31 in the movable magnetic plate 53 away from the manipulation tube 1, and therefore falls by gravity in the recess 72. At this time, the magnetic particles in the manipulation tube 1 receive the influence of the magnetic field of the magnet 31', and therefore can be transported into an aqueous liquid $41_2$ in the recovery part B and fall to near the bottom of the recovery part B together with the magnet 31'. In this way, the magnetic particles are passed from the magnet 31 to the magnet 31' so that the magnetic particles accompanied by a target component can be sufficiently exposed to the lowermost layer in the manipulation tube.

[8-2-5. Magnetic Field Fluctuation]

The magnetic field moving system may have a system that allows fluctuation, such as oscillation or rotation, of a magnetic field. For example, when having the function of allowing the magnetic source to oscillate (vertically move) in the longitudinal direction of the manipulation tube, the magnetic field moving system can be used in place of a stirrer. This makes it possible to easily perform mixing or stirring of the aqueous liquid.

For example, even when the magnetic field moving system does not have the function of blocking or reducing a magnetic field, a target component or the like adsorbed to magnetic particles in the aqueous liquid can be sufficiently exposed to a liquid constituting the aqueous liquid layer by vertically oscillating the magnetic particles several times within a width corresponding to the width or thickness of the aqueous liquid layer in a state where the magnetic field applying means remains close to the manipulation tube (i.e., in a state where the magnetic particles remain agglomerated together).

[8-2-6. Temperature Control Function]

The magnetic field applying means may further have a temperature control function. For example, the temperature control function is schematically shown by a reference sign 42 in FIG. 4. Alternatively, a heater may be contained in the magnetic field applying means. In the latter case, the temperature of a reagent in the aqueous liquid layer, in which magnetic particles are present, can be arbitrarily controlled by the temperature control function.

The temperature control function will be descried with reference to a case where the manipulation tube shown in FIG. 4 is held by the holding means (holding substrate), as shown in FIG. 7, having such a temperature control function as described above in 7-3. In the manipulation tube shown in FIG. 4, the recovery part B accommodates multiple layers including an RT reaction liquid layer $41_1$, a PCR reaction liquid layer $41_2$, and a gel layer $4g$ interposed between said layers as a recovery medium. When the manipulation tube shown in FIG. 4 is held by the holding substrate 51 as shown in FIG. 7, there is a case where only part of the manipulation tube roughly corresponding to the lowermost layer (PCR reaction liquid layer $41_2$) thereof is directly held in the holding hole 52 of the holding substrate 51. In this case, the RT reaction liquid layer $41_1$ in which a reverse transcription reaction is performed is separated from the PCR reaction liquid layer $41_2$ directly held by the holding substrate 51, and therefore it is difficult to control the temperature of the RT reaction liquid layer $41_1$ by the holding substrate 51.

The device according to the present invention may have another temperature control function different from the temperature control function of the holding means. For example, the other temperature control function may be a function, as shown by the reference sign 42 in FIG. 4, which does not move simultaneously with the magnetic field applying means, or may be a function, as shown by a reference sign 64 in FIG. 6, which is contained in the movable magnetic plate 53, which is magnetic field applying means, so as to simultaneously move with the magnetic field applying means. In a specific embodiment of the movable magnetic plate 53 containing the temperature control function (heater) as shown in FIG. 6, the heater 64 has a ring shape so as to surround the holding hole 54. By allowing the movable magnetic plate 53 to have a temperature control function in this way, it is possible to heat the RT reaction liquid by the heater 64 in the movable magnetic plate 53 when the movable magnetic plate 53 is located at a position where the RT reaction liquid layer $41_1$ is accommodated (FIG. 7(1)) to achieve an optimal temperature (e.g., 50° C.).

[9. Optical Detection Means]

The optical detection means is not particularly limited and can be easily selected by those skilled in the art depending on a method of analysis to which a target component is subjected. For example, means appropriately including a light-generating unit, detection means, light-transmitting means, and a personal computer can be used.

One example of such means is as follows. In the case of fluorescence detection means 41 shown in FIG. 4(7), as specifically shown in FIG. 7, the reaction liquid 4 in the manipulation tube 1 can be irradiated with light through the detection lens 44 by allowing light emitted from the light-generating unit (not shown) to enter the light-transmitting means (optical fiber cable 45) attached to the detection means (detection lens 44). An optical signal detected by the detection lens 44 is sent through the optical fiber cable 45 to a light-receiving element, converted to an electrical signal, and then sent to the personal computer (not shown) in real time so that a change in the fluorescence intensity of the reaction liquid 4 can be monitored. This is preferred when the present invention is applied to reaction or treatment, such as real-time nucleic acid amplification reaction, which performs detection of variable fluorescence intensity.

Examples of the light-generating unit include an LED, a laser, and a lamp. In detection, various light-receiving elements from inexpensive photodiodes to more sensitive photomultipliers can be used without any particular limitation.

For example, when nucleic acid-associated reaction, such as a real-time nucleic acid amplification reaction, or nucleic acid-associated treatment is performed using, for example, SYBR (registered trademark) GREEN I, this dye specifically binds to double-stranded DNA and emits fluorescence at around 525 nm, and therefore light having a wavelength of interest can be detected by the detection means by cutting off light other than the light having a wavelength of interest with the use of an optical filter.

Further, for example, when a nucleic acid amplification reaction is performed by moving a droplet in the manipulation tube, the fluorescence of the droplet subjected to a nucleic acid amplification reaction can be observed in a dark room by irradiating a point having temperature at which an extension reaction by DNA polymerase is performed (usually, about 68 to 74° C.) with excitation light in a state where the droplet is stopped at the point. Further, by expanding a range irradiated with excitation light from a point having temperature at which thermal denaturation is performed to a point having temperature at which annealing is performed, a melting curve of an amplified product can be obtained by moving the droplet.

EXAMPLES

The present invention will be described in more detail with reference to examples, but is not limited thereto.

Example 1

Extraction/Purification of Nucleic Acid from Blood

A gelating agent (TAISET 26 manufactured by Taiyo Kagaku Co., Ltd.) was added to silicone oil (KF-56 manufactured by Shin-Etsu Silicone) at 1.2% (weight ratio) and heated to 70° C. to be completely mixed with the silicone oil. The required amounts of the oil put into a sol state by mixing and a necessary reagent were alternately injected into a manipulation tube shown in FIG. 3(0) (constituted from a capillary (manipulation part A) and a sample tube (recovery part B)) through the tip of a syringe needle without trapping air bubbles to form multiple layers. When the capillary had an inner diameter of 1.5 mm, as shown in FIG. 3(0), each gel plug was formed by charging 10 µL of the oil, each washing liquid layer was formed by charging 15 µL of a washing liquid (200 mM KCl), and an eluent layer was formed by charging 20 µL of an eluent (10 mM Tris HCl, 1 mM EDTA pH 8.0). After the charging was completed, the capillary was allowed to stand at room temperature for 30 minutes to completely gelate the gel plugs. The capillary had, at its upper end, a funnel-like sample supply port sealed with a film material, and was hermetically sealed with a septum.

An uppermost layer in the capillary was composed of 100 of a cell lysis liquid (4M guanidinium thiocyanate, 2% (w/v) Triton X-100, and 100 mM Tris-HCl pH 6.3) and contained 500 µg of silica-coated magnetic particles (magnetic particles supplied with a nucleic acid extraction kit, TOYOBO MagExtractor-Plasmid-). It is to be noted that a method for isolating nucleic acid using silica particles and a chaotropic salt (JP-A-H02-289596) disclosed by Boom et al was used.

FIGS. 3(1) to 3(14) show the manipulation of a magnet in the process of extracting nucleic acid from blood. Finally, nucleic acid is recovered in the eluent in the sample tube attached to the lower end of the capillary.

In FIG. 3(1), 200 µL of human whole blood was injected with a syringe needle and lightly mixed with the magnetic particles by pipetting. After 5 minutes, as shown in FIGS. 3(2) and (3), the magnet was moved closer to the side surface of the capillary to collect the magnetic particles and was then moved downward at a rate of 0.5 mm/second. After the magnetic particles were passed through the gel plug, as shown in FIG. 3(4), the magnet was moved away from the capillary. The magnetic particles were washed three times in the same manner as shown in FIGS. 3(5) to 3(12). Then, as shown in FIG. 3(13), the magnet was moved away from the capillary to drop the magnetic particles into the tube containing the eluent. After one minute, the magnet was again moved closer to the tube to collect the magnetic particles, and as shown in FIG. 3(14), the magnetic particles were moved back into the gel plug to complete the manipulation of extraction/purification of nucleic acid. In this example, 200 ng of DNA was obtained per 1 microliter of eluent.

Figure 8:
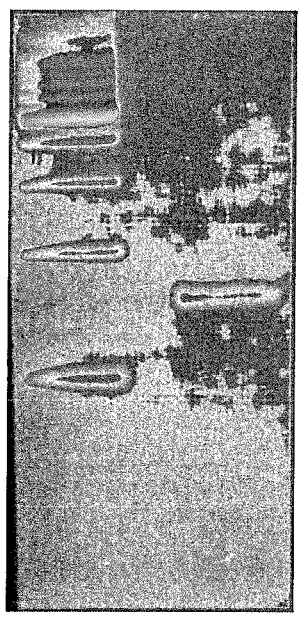
FIG. 8 shows a result obtained in Example 1 in which the process shown in FIG. 3 was performed.

The sample tube was detached from the capillary, and 1 of the eluent in the sample tube was used to perform PCR (temperature cycle: 40 cycles of 95° C. for 1 second, 60° C. for 10 seconds, and 72° C. for 10 seconds) in a thermal cycler (ABI 9700 manufactured by Applied Biosystems) using a PCR reaction mixture containing 0.15 U Taq DNA polymerase, 500 nM each primer for detecting human GAPDH gene (5'-GCGCTGCCAAGGCT-GTGGGCAAGG-3' (SEQ ID No. 1) and 5'-GGCCCTC-CGACGCCTGCTTCACCA-3' (SEQ ID No. 2)), and 200 nM dNTP (total amount of reaction liquid: 10 µL). As a result, as shown in FIG. 8, a reaction product specific to human GAPDH gene (fragment size: 171 bases) was observed by agarose gel electrophoresis.

Example 2

Detection of Influenza Virus from Nasal Cavity Swab

A manipulation tube (capillary device) shown in FIG. 4(0) was filled with reagents and a gel in the same manner as in Example 1 except that a reverse transcription reaction liquid (RT reaction liquid) and a PCR reaction liquid were further used. The capillary device used in this example was not the capillary device used in Example 1 in which a recovery sample tube was attached to the lower end of a capillary but a capillary device integrally formed to have a blind lower end. By covering a sample supply port of this capillary device with a septum, a completely hermetically sealed PCR device with nucleic acid extraction function is obtained. Detection was performed by fluorescence detection using a fluorescent dye such as SYBR Green I based on a real-time detection method or an end-point detection method.

During nucleic acid extraction in the capillary device shown in FIG. 4, sample addition and magnet manipulation were performed in the same manner as shown in FIGS. 3(1) to 3(12) (FIGS. 4(1) to 4(5)). Influenza virus particles (100 particles) were added to 200 µL of a nasal cavity swab prepared as a sample to determine whether or not a viral gene could be detected in the sample by RT-PCR. The genome of the influenza virus is RNA, and therefore the RNA needs to be converted to DNA in order to detect the viral gene by PCR. For this reason, prior to PCR, reaction using a reverse transcription enzyme was performed. In a state shown in FIG. 4(6), nucleic acid containing viral RNA is adsorbed to the surfaces of the magnetic particles. The viral RNA was converted to DNA by a reverse transcription enzyme and a reverse transcription primer.

The composition of the reverse transcription reaction liquid used in this example was determined according to the manual of SuperScript III Reverse Transcriptase manufactured by Invitrogen. As the primer, 50 ng of a random hexamer (Roche) was used. The amount of the reaction liquid was 10 µL. The reaction was performed by keeping the magnet away from the capillary to disperse the magnetic particles in the reaction liquid and then performing incubation at 25° C. for 5 minutes and then at 50° C. for 5 minutes. After the completion of the reverse transcription reaction, the magnetic particles were again collected by the magnet and moved into the PCR reaction liquid as a lowermost end. Then, the temperature cycles of PCR were performed. Simultaneously as the temperature cycles, the capillary device was irradiated with light emitted from a 470 nm LED light source from the bottom of the temperature adjustment block to monitor 520 nm fluorescence from SYBR Green I specific to a PCR product.

Figure 9:
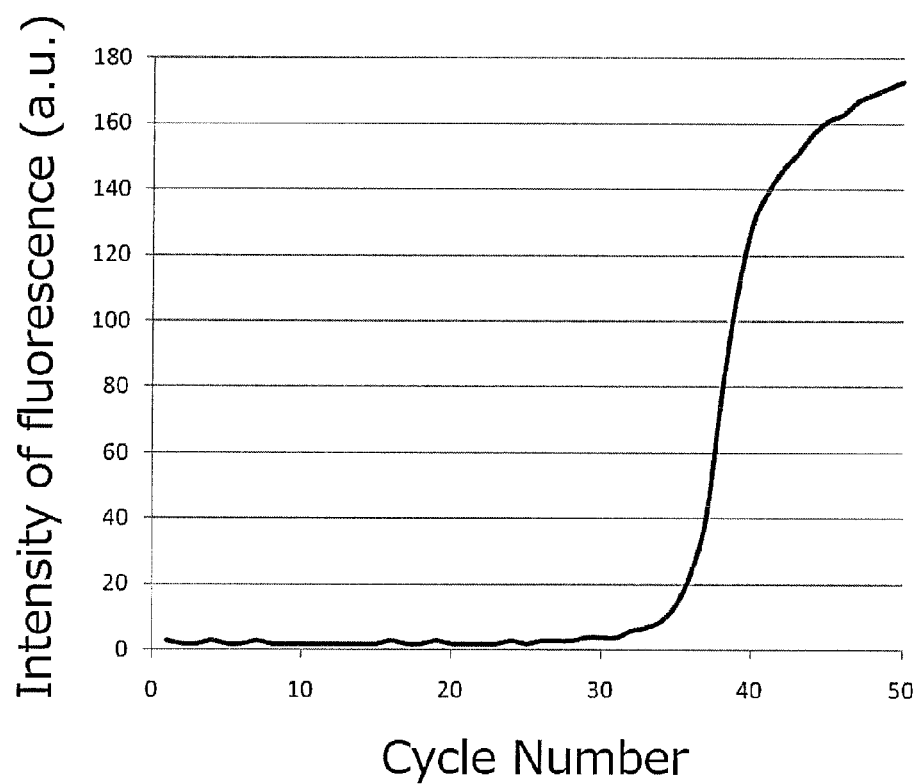
FIG. 9 shows a result obtained in Example 2 in which the process shown in FIG. 4 was performed.

The PCR reaction liquid used in this example had the following composition: 25 mM Tris-HCl pH 8.3, 10 mM MgCl$_2$, 0.2% (w/v) BSA, 1 mM dNTP, 0.5 μM each primer for detecting influenza virus A (5'-GACCRATCCTGTCAC-CTCTGAC-3' (SEQ ID No. 3) and 5'-AGGGCATTYTG-GACAAAKCGTCTA-3' (SEQ ID No. 4)), and 0.1 U/μL Ex Taq DNA polymerase (TAKARA BIO INC.). The amount of the PCR reaction liquid was 5 μL. The PCR consisted of 50 temperature cycles of 95° C. for 1 second and 68° C. for 10 seconds. The fluorescence measurement was performed using a cooled CCD camera by exposure to light for 3 seconds during the extension reaction at 68° C. The image data was digitized using analysis software "Image J", and the results are shown in FIG. 9. As shown in FIG. 9, an increase in the intensity of fluorescence specific to SYBR Green I is observed at around 35 cycles, from which it can be seen that the influenza virus gene was amplified and detected.

The present invention has been described above with reference to the embodiments of the present invention, but it should not be understood that the description and drawings constituting part of the disclosure limit the present invention. From the disclosure, various alternate embodiments, examples, and operation techniques will be apparent to those skilled in the art. The technical scope of the present invention is defined only by the matters specifying the invention according to the claims reasonable from the above description, and various modifications can be made in the implementation stage without departing from the scope of the present invention.

DESCRIPTION OF REFERENCE SIGNS

1: Manipulation tube
2g: Gel layer (gel plug)
3: Manipulation medium (multiple layers)
31: Aqueous liquid layer
3g: Gel layer (gel plug)
4: Recovery medium (e.g., eluent, reaction liquid)
41: Aqueous liquid layer
4g: Gel layer (gel plug)
5: Sample supply portion (open end)
6: Magnetic particles
31: Magnetic field applying means (magnet)
32: Sample
33: Aqueous liquid mixture
41: Optical detection means
42, 43: Temperature control function (heater)
51: Holding means (temperature adjustment block)
52: Holding hole
53: Magnetic field applying means (movable magnetic plate)
54: Holding hole
61: Magnet holding portion
64: Temperature control function (heater)
71: Optical detection port
72: Recess

SEQUENCE LISTING FREE TEXT

SEQ ID Nos. 1 to 4 represent synthetic primers.

The invention claimed is:

1. A device for manipulating a target component in a manipulation tube, comprising:
   a manipulation tube comprising a tube having an optionally-closeable open end for supplying a sample containing a target component at one end and a closed end at the other end, and a manipulation medium accommodated in the tube and having a gel layer and an aqueous liquid layer alternately layered in a longitudinal direction of the tube, wherein the gel layer is a gel plug provided on either side of the aqueous liquid layer so that the aqueous liquid layer is sandwiched between the gel plugs in the longitudinal direction of the tube, and is fixed in a predetermined position in the tube;
   magnetic particles that should capture and transport the target component; and
   a magnetic field applying member capable of applying a magnetic field to the manipulation tube to move the magnetic particles in the longitudinal direction of the manipulation tube through the gel layer in a gel state.

2. The device according to claim 1, wherein the tube has an approximate inner diameter of 0.1 mm to 5 mm.

3. The device according to claim 1, wherein the magnetic field applying member can move the magnetic particles in the longitudinal direction of the manipulation tube from an outside position of the manipulation tube.

4. The device according to claim 1, further comprising a holding member capable of holding the manipulation tube almost vertically in such a manner that the open end faces upward.

5. The device according to claim 4, wherein the holding member is a holding substrate having a plurality of holding holes capable of holding the closed end of the manipulation tube.

6. The device according to claim 4, wherein the holding member has a temperature control function.

7. The device according to claim 4, wherein the holding member has a recess allowing the magnetic field applying member to be moved in the longitudinal direction of the manipulation tube.

8. The device according to claim 4, wherein the holding member has an optical detection port.

9. The device according to claim 1, wherein the magnetic field applying member has a system that controls movement of a magnetic field in the longitudinal direction of the manipulation tube and strength of the magnetic field.

10. The device according to claim 1, wherein the magnetic field applying member has a temperature control function.

11. The device according to claim 9, wherein the magnetic field applying member comprises a movable substrate capable of moving in the longitudinal direction of the manipulation tube, and a plurality of magnetic sources held in the movable substrate.

12. The device according to claim 11, wherein the system that controls movement of a magnetic field in the longitudinal direction of the manipulation tube and strength of the magnetic field simultaneously moves the plurality of magnetic sources in the movable substrate.

13. The device according to claim 1, wherein the magnetic particles have an ability to bind to or adsorb to nucleic acid as the target component, and the manipulation medium includes an aqueous liquid layer composed of a liquid that liberates the nucleic acid to bind or adsorb the nucleic acid to the magnetic particles and/or an aqueous liquid layer composed of a liquid for washing the magnetic particles.

14. The device according to claim 13, wherein the manipulation medium further includes an aqueous liquid layer composed of a nucleic acid amplification reaction liquid; or an aqueous liquid layer composed of a reverse transcription reaction liquid and an aqueous liquid layer composed of a nucleic acid amplification reaction liquid.

15. The device according to claim 1, wherein the tube is integrally formed.

16. The device according to claim 1, wherein
   the manipulation tube has a manipulation part A and a recovery part B;
   the tube constituting the manipulation tube has a manipulation tube portion a and a recovery tube portion b corresponding to the manipulation part A and the recovery part B, respectively;
   the manipulation part A comprises the tube portion a, and the manipulation medium accommodated in the tube portion a; and
   the recovery part B comprises the tube portion b, and a recovery medium accommodated in the tube portion b and including at least one of an aqueous liquid layer and a gel layer.

17. The device according to claim 16, wherein the manipulation tube portion a and the recovery tube portion b are separable from each other.

18. The device according to claim 1, wherein the tube is made of a material selected from the group consisting of polyethylene, polypropylene, fluorine resin, polyvinyl chloride, polystyrene, polycarbonate, acrylonitrile butadiene styrene copolymer, acrylonitrile styrene copolymer, acrylic resin, polyvinyl acetate, polyethylene terephthalate, cyclic polyolefin, and glass.

19. A manipulation tube for manipulating a target component, comprising:

a tube having an optionally-closeable open end for supplying it sample containing a target component at one end and a closed end at the other end;

a manipulation medium accommodated in the tube and having a gel layer and an aqueous liquid layer alternately layered in a longitudinal direction of the tube, wherein the gel layer is a gel plug provided on either side of the aqueous liquid layer so that the aqueous liquid layer is sandwiched between the gel plugs in the longitudinal direction of the tube, and is fixed in a predetermined position in the tube; and magnetic, particles that should capture and transport the target component, wherein the manipulation tube is constituted so that the magnetic particles are moved in the longitudinal direction of the manipulation tube through the gel layer in a gel state by applying a magnetic field to the manipulation tube.

* * * * *